(12) United States Patent
Sidera et al.

(10) Patent No.: US 9,115,192 B2
(45) Date of Patent: Aug. 25, 2015

(54) COMPOSITIONS AND METHODS FOR TREATING NEOPLASIA

(71) Applicant: Zestagen S.A., Epalignes (CH)

(72) Inventors: Katerina Sidera, Athens (GR); Avgi Mamalaki, Athens (GR); Evangelia Patsavoudi, Athens (GR)

(73) Assignee: Zestagen S.A., Epalignes (CH)

( * ) Notice: Subject to any disclaimer, the term of this patent is extended or adjusted under 35 U.S.C. 154(b) by 0 days.

(21) Appl. No.: 13/797,194

(22) Filed: Mar. 12, 2013

(65) Prior Publication Data

US 2013/0280244 A1   Oct. 24, 2013

Related U.S. Application Data

(63) Continuation-in-part of application No. PCT/EP2011/066791, filed on Sep. 27, 2011.

(60) Provisional application No. 61/386,764, filed on Sep. 27, 2010.

(51) Int. Cl.
*A61K 39/395* (2006.01)
*C07K 16/18* (2006.01)
*A61K 39/00* (2006.01)

(52) U.S. Cl.
CPC ........... *C07K 16/18* (2013.01); *A61K 2039/505* (2013.01); *C07K 2317/24* (2013.01); *C07K 2317/515* (2013.01); *C07K 2317/73* (2013.01)

(58) Field of Classification Search
None
See application file for complete search history.

(56) References Cited

U.S. PATENT DOCUMENTS

2006/0228349 A1* 10/2006 Acton et al. ............... 424/133.1

OTHER PUBLICATIONS

Rudikoff et al. (Proc. Natl. Acad. Sci. USA, 79(6): 1979-1983).*
McCarthy et al. (J. Immunol. Methods, 251(1-2): 137-149, 2001).*
Dimitris Stellas et al., "Monoclonal antibody 4C5 prevents activation of MMP2 and MMP9 by disrupting their interaction with extracellular HSP90 and inhibits formation of metastatic breast cancer cell deposits", BMC Cell Biology, 2010, 11:51, pp. 1-9.
Stellas Dimitris et al: "Monoclonal antibody 4C5 prevents activation of MMP2 and MMP9 by disrupting their interaction with extracellular HSP90 and inhibits formation of metastatic breast cancer cell deposits". BMC Cell Biology, Biomed Central, London, GB, vol. 11, No. 1, Jul. 5, 2010, p. 51.
K. Sidera et al: "A Critical Role for HSP90 in Cancer Cell Invasion Involves Interaction with the Extracellular Domain of HER-2". Journal of Biological Chemistry, vol. 283, No. 4, Jan. 1, 2007, pp. 2031-2041.
Winter G et al: "Humanized antibodies", Trends in Pharmacolgial Sciences, Elsevier, Haywarth, GB, vol. 14, No. 5, May 1, 1993, pp. 139-143.
Thomaidou D et al: "Identifcation of a novel neuron-specific surface antigen in the developing nervous system, by monoclonal antibody 4C5", Neuroscience, New York, NY, US, vol. 53, No. 3, Apr. 1, 1993, pp. 813-827.
Michael Pech et al: Differences between germ-line and rearranged immunoglobulin V[kappa] coding sequences suggest a localized mutation mechanism, Nature, vol. 291, No. 5817, Jun. 25, 1981, pp. 668-670.
Jul. 21, 1986, "RecName: Full=Ig kappa chain V-V region L6; Flags: Precursor; Fragment", XP002662639, retrieved from EBI accession No. UNIPROT: P01638, Database accession No. P01638 sequence.
Katerina Sidera et al: "The 4C5 Cell-Impermeable Anti-HSP90 Antibody with Anti-Cancer Activity, Is Composed of a Single Light Chain Dimer", PLOS ONE, vol. 6, No. 9, Jan. 1, 2011, p. E23906.
International Search Report for PCT/EP2011/066791, Nov. 15, 2011, 4 pages.

* cited by examiner

*Primary Examiner* — Brad Duffy
*Assistant Examiner* — Nelson B Moseley, II
(74) *Attorney, Agent, or Firm* — Saul Ewing LLP; Peter C. Lauro, Esq.; Elbert Chiang

(57) ABSTRACT

The invention provides therapeutic methods featuring the use of chimeric human/mouse antibodies for the treatment of neoplasia.

22 Claims, 10 Drawing Sheets

IP: anti-HSP90α imput imput control   mAb4C5 treated

SEQUENCE LISTING

<160> NUMBER OF SEQ ID NOS: 23

<210> SEQ ID NO 1
<211> LENGTH: 645
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1

```
gagctcgtca tgacccagtc tccatcttcc atgtatgcat ctctaggaga gagagtcact      60
atcacttgca aggcgagtca ggacattaat agctatttaa gctggttcca gcagaaacca     120
gggaaatctc ctaagaccct gatctatcgt gcaaacagat tggtagatgg ggtcccatca     180
aggttcagtg gcagtggatc tgggcaagat tattctctca ccatcaacag cctggagtat     240
gaagatatgg gaatttatta ttgtctacag tatgatgagt ttcctcggct cacgttcggt     300
gctgggacca ggctggagct gaaacgggct gatgctgcac caactgtatc catcttccca     360
ccatccagtg agcagttaac atctggaggt gcctcagtcg tgtgcttctt gaacaacttc     420
tatcccaaag acatcaatgt caagtggaag attgatggca gtgaacgaca aaatggcgtc     480
ctgaacagtt ggactgatca ggacagcaaa gacagcacct acagcatgag cagcaccctc     540
acgttgacca aggacgagta tgaacgacat aacagctata cctgtgaggc cactcacaag     600
acatcaactt cacccattgt caagagcttc aacaggaatg agtgt                     645
```

<210> SEQ ID NO 2
<211> LENGTH: 215

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Leu Val Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Asn Ser Leu Glu Tyr
65                  70                  75                  80

Glu Asp Met Gly Ile Tyr Tyr Cys Leu Gln Tyr Asp Glu Phe Pro Arg
                85                  90                  95

Leu Thr Phe Gly Ala Gly Thr Arg Leu Glu Leu Lys Arg Ala Asp Ala
            100                 105                 110

Ala Pro Thr Val Ser Ile Phe Pro Pro Ser Ser Glu Gln Leu Thr Ser
        115                 120                 125

Gly Gly Ala Ser Val Val Cys Phe Leu Asn Asn Phe Tyr Pro Lys Asp
130                 135                 140

Ile Asn Val Lys Trp Lys Ile Asp Gly Ser Glu Arg Gln Asn Gly Val
145                 150                 155                 160

Leu Asn Ser Trp Thr Asp Gln Asp Ser Lys Asp Ser Thr Tyr Ser Met
                165                 170                 175

Ser Ser Thr Leu Thr Leu Thr Lys Asp Glu Tyr Glu Arg His Asn Ser
            180                 185                 190

Tyr Thr Cys Glu Ala Thr His Lys Thr Ser Thr Ser Pro Ile Val Lys
        195                 200                 205

Ser Phe Asn Arg Asn Glu Cys
    210                 215

<210> SEQ ID NO 3
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
gagctcgtca tgacccagtc tccatcttcc atgtatgcat ctctaggaga gagagtcact      60
atcacttgca aggcgagtca ggacattaat agctatttaa gctggttcca gcagaaacca     120
gggaaatctc ctaagaccct gatctatcgt gcaaacagat ggtagatgg gtcccatca      180 aggttcagtg gcagtggatc tgggcaagat tattctctca ccatcaacag cctggagtat     240
gaagatatgg gaatttatta ttgtctacag tatgatgagt ttcctcggct cacgttcggt     300
gctgggacca ggctggagct gaaacgaact gtggctgcac catctgtctt catcttcccg     360
ccatctgatg agcagttgaa atctgggact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540

```
acgctgagca aagcagacta cgagaaacac aaagtctacg cctgcgaagt cacccatcag    600
ggcctgagtt cgcccgtcac aaagagcttc aacaggggag agtgt                   645
```

```
<210> SEQ ID NO 4
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4
```

Glu Leu Val Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Asn Ser Leu Glu Tyr
65                  70                  75                  80

Glu Asp Met Gly Ile Tyr Tyr Cys Leu Gln Tyr Asp Glu Phe Pro Arg
                85                  90                  95

Leu Thr Phe Gly Ala Gly Thr Arg Leu Glu Leu Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

```
<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5
```

Lys Ala Ser Gln Asp Ile Asn Ser Tyr Leu Ser
1               5                   10

```
<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 6

Arg Ala Asn Arg Leu Val Asp
1               5

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Leu Gln Tyr Asp Glu Phe Pro Arg Leu Thr
1               5                   10

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N,N-dimethyl-L-valyl
<220> FEATURE:
<221> NAME/KEY: MOD_RES
<222> LOCATION: (2)..(2)
<223> OTHER INFORMATION: L-valyl
<220> FEATURE:
<221> NAME/KEY: MOD_RES
<222> LOCATION: (3)..(3)
<223> OTHER INFORMATION: N-methyl-L-valyl
<220> FEATURE:
<221> NAME/KEY: MOD_RES
<222> LOCATION: (4)..(4)
<223> OTHER INFORMATION: L-prolyl
<220> FEATURE:
<221> NAME/KEY: MOD_RES
<222> LOCATION: (5)..(5)
<223> OTHER INFORMATION: 1-L-prolyl-t-butylamide

<400> SEQUENCE: 8

Val Val Val Pro Pro
1               5

<210> SEQ ID NO 9
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
gagctcgtca tgacccagag cccgagcagc atgtatgcaa gcctgggcga acgtgtgacc      60
atcacctgca aagcgagcca ggatattaat agctatctgt cttggtttca gcagaaaccg     120
ggcaaaagcc cgaaaaccct gatttatcgt gcaaaccgtc tggtagatgg cgtgccgtca     180
cgttttagcg gttctggcag cggccaggat tatagcctga ccattaacag cctgaatat     240 gaagatatgg gcatttatta ttgcctgcag tatgatgaat tccgcgtctg acgtttggc     300 gcgggcaccc gtctggaact gaaacgtacc gttgcggcac cgagcgtgtt tatttttccg     360
ccgagcgatg aacagctgaa aagtggcacc gcgagcgttg tgtgcctgct gaataacttt     420

```
tatccgcgtg aagccaaagt acagtggaaa gtggataacg ccctgcagag cggcaacagc      480
caggaaagcg tgaccgaaca ggatagcaaa gatagcacct atagcctgtc tagcaccctg      540
acgctgagca aagcagatta tgaaaaacat aaagtgtatg cctgcgaagt gacccatcag      600
ggcctgagca gcccggtgac caaaagcttt aatcgtggcg aatgc                      645
```

<210> SEQ ID NO 10
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

```
gagctcgtca tgacccagag cccgagcagc atgtatgcaa gcctgggcga acgtgtgacc      60
atcacctgca aagcgagcca ggatattaat agctatctgt cttggtttca gcagaaaccg      120
ggcaaaagcc cgaaaaccct gatttatcgt gcaaaccgtc tggtagatgg cgtgccgtca      180
cgttttagcg gttctggcag cggccaggat tatagcctga ccattaacag cctggaatat      240
gaagatatgg gcatttatta ttgcctgcag tatgatgaat tccgcgtctc gacgtttggc      300
gcgggcaccc gtctggaact gaaacgtacc gttgcggcac cgagcgtgtt tatttttccg      360
ccgagcgatg aacagctgaa aagtggcacc gcgagcgttg tgtgcctgct gaataacttt      420
tatccgcgtg aagccaaagt acagtggaaa gtggataacg ccctgcagag cggcaacagc      480
caggaaagcg tgaccgaaca ggatagcaaa gatagcacct atagcctgtc tagcaccctg      540
acgctgagca aagcagatta tgaaaaacat aaagtgtatg cctgcgaagt gacccatcag      600
ggcctgagca gcccggtgac caaaagcttt aatcgtggcg aa                        642
```

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11

```
aggcttacta gtacaatccc tgggcacaat                                       30
```

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12

```
aggtccagct gctcgagtct gg                                               22
```

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13

```
aggtccagct gctcgagtca gg                                               22
```

```
<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
aggtccagct tctcgagtct gg                                              22

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
aggtccagct tctcgagtca gg                                              22

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
aggtccaact gctcgagtct gg                                              22

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
aggtccaact gctcgagtca gg                                              22

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
aggtccaact tctcgagtct gg                                              22

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
aggtccaact tctcgagtca gg                                              22
```

<210> SEQ ID NO 20
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
gcgccgtcta gaattaacac tcattcctgt tgaa         34

<210> SEQ ID NO 21
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
ccagatgtga gctcgtcatg acccagtctc ca           32

<210> SEQ ID NO 22
<211> LENGTH: 324
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(324)

<400> SEQUENCE: 22 gag ctc gtc atg acc cag tct cca tct tcc atg tat gca tct cta gga       48
Glu Leu Val Met Thr Gln Ser Pro Ser Ser Met Tyr Ala Ser Leu Gly
1               5                   10                  15 gag aga gtc act atc act tgc aag gcg agt cag gac att aat agc tat       96
Glu Arg Val Thr Ile Thr Cys Lys Ala Ser Gln Asp Ile Asn Ser Tyr
            20                  25                  30 tta agc tgg ttc cag cag aaa cca ggg aaa tct cct aag acc ctg atc      144
Leu Ser Trp Phe Gln Gln Lys Pro Gly Lys Ser Pro Lys Thr Leu Ile
        35                  40                  45 tat cgt gca aac aga ttg gta gat ggg gtc cca tca agg ttc agt ggc      192
Tyr Arg Ala Asn Arg Leu Val Asp Gly Val Pro Ser Arg Phe Ser Gly
    50                  55                  60 agt gga tct ggg caa gat tat tct ctc acc atc aac agc ctg gag tat      240
Ser Gly Ser Gly Gln Asp Tyr Ser Leu Thr Ile Asn Ser Leu Glu Tyr
65                  70                  75                  80 gaa gat atg gga att tat tat tgt cta cag tat gat gag ttt cct cgg      288
Glu Asp Met Gly Ile Tyr Tyr Cys Leu Gln Tyr Asp Glu Phe Pro Arg
                85                  90                  95 ctc acg ttc ggt gct ggg acc agg ctg gag ctc aaa                      324
Leu Thr Phe Gly Ala Gly Thr Arg Leu Glu Leu Lys
            100                 105

<210> SEQ ID NO 23
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 23

-continued

```
Glu Leu Val Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
                20              25                  30

Leu Ser Trp Phe Gln Gln Lys Pro Gly Lys Ser Pro Lys Thr Leu Ile
            35              40              45

Tyr Arg Ala Asn Arg Leu Val Asp Gly Val Pro Ser Arg Phe Ser Gly
    50              55              60

Ser Gly Ser Gly Gln Asp Tyr Ser Leu Thr Ile Asn Ser Leu Glu Tyr
65              70              75                  80

Glu Asp Met Gly Ile Tyr Tyr Cys Leu Gln Tyr Asp Glu Phe Pro Arg
            85              90              95

Leu Thr Phe Gly Ala Gly Thr Arg Leu Glu Leu Lys
            100             105
```

COMPOSITIONS AND METHODS FOR TREATING NEOPLASIA

CROSS-REFERENCE TO RELATED APPLICATIONS

This application is a continuation-in-part of international patent application No. PCT/EP2011/066791, filed Sep. 27, 2011, that was published in English on Apr. 5, 2012 as publication No. WO 2012/041863 A1, and claims the benefit of U.S. Provisional Application No. 61/386,764, filed Sep. 27, 2010. The entire contents of the aforementioned patent applications are incorporated herein by reference.

SEQUENCE LISTING

The instant application contains a Sequence Listing which has been submitted in ASCII format via EFS-Web and is hereby incorporated by reference in its entirety. Said ASCII copy, created on Jun. 27, 2013, is named 313200.00013_SL.txt and is 14,948 bytes in size.

BACKGROUND OF THE INVENTION

Monoclonal antibody (mAb) 4C5 is a murine antibody that specifically recognizes both the a and to a lesser extent the β isoforms of the heat shock protein 90 (HSP90). Recently, HSP90 has become a very attractive drug-target for cancer therapy because most of its client proteins are considered to be key molecules in the acquisition of the malignant phenotype. Moreover, emerging data demonstrating the presence of this molecular chaperone at the surface of cancer cells suggest a wide-ranging phenomenon of extracellular chaperoning implicated in cancer cell invasion and metastasis.

MAb 4C5 was initially shown to inhibit cell migration processes in vitro during development of the nervous system by affecting actin cytoskeletal rearrangement and the formation of motile structures, such as lamellipodia. mAb 4C5 selectively binds to the surface pool of HSP90, and significantly reduces melanoma cell invasion and metastasis. Furthermore, mAb 4C5 was shown to inhibit the extracellular interaction between HSP90 and the growth factor receptor HER-2 in MDAMB453 breast cancer cells, leading to impaired downstream signalling and reduced cancer cell motility and invasion. Finally, mAb 4C5 was shown to inhibit a functional interaction between secreted HSP90 and pro-MMP2 and pro-MMP9, necessary for the activation of these enzymes which is essential for ECM degradation and cancer cell invasion and extravasation.

These combined data suggested that the capacity of mAb 4C5 to specifically inhibit the extracellular pool of HSP90 without affecting the wide range of important intracellular roles of this molecular chaperone could have clinical benefits in the treatment of human malignancies. However, murine mAbs do not constitute ideal therapeutic agents. An obvious problem with the use of murine mAbs in human clinical trials is the potential for the generation of human anti-mouse antibody responses. Initial attempts to use murine-derived mAbs in human therapeutics were hampered because murine antibodies were recognized by a human anti-murine-antibody immune response (HAMA) and the patient's immune system cut short the therapeutic window. These obstacles have been overcome by the advent of recombinant DNA technologies, which have led to the development of chimeric or humanized antibodies.

SUMMARY OF THE INVENTION

As described below, the present invention provides therapeutic compositions and methods for the treatment of neoplasia. In particular embodiments, the present invention provides chimeric human/mouse antibodies for use in the treatment of neoplasia. Because such antibodies are largely human in composition they have a reduced capacity to induce an immune response in a human subject, relative to conventional murine antibodies.

In one aspect, the invention provides an isolated chimeric antibody comprising a murine kappa L-chain that lacks heavy chains, where the murine immunoglobulin κ light chain constant domain ($C_K$) is replaced with the corresponding human $C_K$ domain or a fragment thereof, where the antibody specifically binds HSP90 and is capable of reducing the growth and/or the invasiveness of a neoplastic cell. In one embodiment, the murine kappa L-chain has at least 75%, 85%, 90% or 95% identity to SEQ ID NO: 2. In another embodiment, the murine kappa L-chain contains SEQ ID NO: 2. In another embodiment, the murine kappa L-chain contains one or more murine complementarity determining region. In another embodiment, the murine complementarity determining region has at least 75%) identity to SEQ ID NO: 5, 6, or 7. In another embodiment, the murine light chain contains one or more complementarity determining regions (CDRs) that is SEQ ID NO: 5, 6, and/or 7. In another embodiment, the murine light chain contains complementarity determining regions (CDRs) SEQ ID NO: 5, 6, and 7. In another embodiment, the antibody has at least 75%, 85%, 95% or more amino acid sequence identity to SEQ ID NO:4.

In another aspect, the invention features an isolated chimeric antibody containing or consisting essentially of SEQ ID NO: 4. In one embodiment, the antibody is a humanized antibody. In another embodiment, the antibody is a monomer, a dimer, or a multimer. In another embodiment, the antibody is isolated from a culture of prokaryotic or eukaryotic cells. In various embodiments of the above aspects, the chimeric antibody has a reduced capacity to induce an immune response in a human subject, relative to a conventional murine antibody.

In still other embodiments of the above aspects, the ability of the antibody or a fragment thereof to reduce growth and invasiveness is assayed using a cancer cell clonogenic assay, a wound healing assay, a lung metastatic deposit formation assay, a lung metastasis inhibition assay, a breast cancer primary tumor growth inhibition assay, by detecting actin rearrangement, lamellipodia development or another morphological marker of invasiveness, by detecting inhibition of metastatic lung deposits, by detecting inhibition of lung metastasis, by detecting delay of primary growth tumors implanted orthotopically in mouse fat pads, or by detecting another marker of efficacy, respectively.

In another aspect, the invention features an isolated polypeptide containing the sequence of SEQ ID NO: 4.

In another aspect, the invention features an isolated polynucleotide encoding the chimeric antibody of any previous aspect.

In another aspect, the invention features an isolated polynucleotide encoding the chimeric antibody of a previous aspect or the isolated polypeptide of the previous aspect. In one embodiment, the polynucleotide has the sequence of SEQ ID NO:3.

In another aspect, the invention features an expression vector containing the polynucleotide of any previous aspect positioned for expression in a cell.

In another aspect, the invention features a cell (e.g., a prokaryotic or eukaryotic cell) containing that expression vector.

In another aspect, the invention features a method for producing the chimeric antibody of the invention, the method containing culturing a cell containing an expression vector of the invention under conditions suitable for expression of the chimeric antibody, and isolating the chimeric antibody from the cultured cell.

In another aspect, the invention features a method of reducing the growth and/or invasiveness of a neoplastic cell, the method involving contacting a neoplastic cell with a chimeric antibody of any previous aspect or otherwise delineated herein, thereby reducing the growth and/or invasiveness of the neoplastic cell.

In another aspect, the invention features a method of treating a subject having a neoplasia, the method involving administering to a subject a therapeutically effective amount of the chimeric antibody of any previous aspect or otherwise delineated herein, thereby treating the subject.

In another aspect, the invention features a method of treating or preventing tumor progression or metastasis in a subject having a neoplasia, the method involving administering to a subject a therapeutically effective amount of the chimeric antibody of any previous aspect or otherwise delineated herein, thereby treating or preventing tumor progression or metastasis in the subject. In one embodiment, the neoplastic cell is a cancer cell or is present in a tumor. In another embodiment, the cancer is breast cancer, melanoma, glioblastomas, colon cancer, non-small cell lung cancer or lymphoma. In another embodiment, the chimeric antibody is administered systemically or locally. In another embodiment, the chimeric antibody is a monomer, a dimer or a multimer. In another embodiment, the chimeric antibody is covalently linked to a functional moiety. In another embodiment, the functional moiety is radioactive or is a chemotherapeutic agent.

In another embodiment, the method further involves administering to a subject a therapeutically effective amount of one or more chemotherapeutics. In various embodiments of the above aspects, one or more chemotherapeutics is selected from any one or more of the following: abiraterone acetate, altretamine, anhydro vinblastine, auristatin, bexarotene, bicalutamide, BMS 184476, 2,3,4,5,6-pentafluoro-N-(3-fluoro-4-methoxyphenyl)benzene sulfonamide, bleomycin, N,N-dimethyl-L-valyl-L-valyl-N-methyl-L-valyl-L-proly-1-Lproline-t-butylamide (SEQ ID NO: 8), cachectin, cemadotin, chlorambucil, cyclophosphamide, 3',4'-didehydro-4'-deoxy-8'-norvin- caleukoblastine, docetaxol, doxetaxel, cyclophosphamide, carboplatin, carmustine (BCNU), cisplatin, cryptophycin, cyclophosphamide, cytarabine, dacarbazine (DTIC), dactinomycin, daunorubicin, decitabine dolastatin, doxorubicin (adriamycin), etoposide, 5-fluorouracil, finasteride, flutamide, hydroxyurea and hydroxyureataxanes, ifosfamide, liarozole, lonidamine, lomustine (CCNU), MDV3100, mechlorethamine (nitrogen mustard), melphalan, mivobulin isethionate, rhizoxin, sertenef, streptozocin, mitomycin, methotrexate, 5-fluorouracil, nilutamide, onapristone, paclitaxel, prednimustine, procarbazine, RPRI 09881, stramustine phosphate, tamoxifen, tasonermin, taxol, tretinoin, vinblastine, vincristine, vindesine sulfate, and vinflunine.

In various embodiments of the above aspects, the chimeric antibody has a reduced capacity to induce an immune response in a human subject, relative to a conventional murine antibody.

In another aspect, the invention features a pharmaceutical composition for the treatment of neoplasia comprising a therapeutically effective amount of the chimeric antibody of any previous aspect or otherwise delineated herein. In another aspect, the invention features a pharmaceutical composition for the treatment of neoplasia comprising a therapeutically effective amount of an isolated polypeptide comprising SEQ ID NO: 4.

In another aspect, the invention features a pharmaceutical composition for the treatment of neoplasia comprising a therapeutically effective amount of an isolated polypeptide comprising one or more complementarity determining regions selected from SEQ ID NO: 5, SEQ ID NO: 6, and SEQ ID NO: 7.

In another aspect, the invention features a kit for the treatment of a neoplasia, the kit comprising a therapeutically effective amount of the chimeric antibody of any previous aspect or otherwise delineated herein or an isolated polypeptide comprising a sequence selected from SEQ ID SEQ ID NO: 4, SEQ ID NO: 5, SEQ ID NO: 6, SEQ ID NO: 7 SEQ ID NO: 8, SEQ ID NO: 8, and SEQ ID NO: 7; and directions for using the kit in a method of any previous aspect.

BRIEF DESCRIPTION OF THE DRAWINGS

FIG. 1 A is a western blot of mAb 4C5 run under reducing and non-reducing conditions and probed with antibodies specific for the mouse kappa chain, mouse Fab, and Fcγ. Purified mAb 4C5 isolated from hybridoma cultures was subjected to SDS-PAGE electrophoresis under reducing and non-reducing conditions, followed by immunoblotting with an anti-mouse kappa chain, an anti-mouse Fab, and an anti-Fcγantibody. Under reducing electrophoresis followed by western blot with the anti-Fab antibody, a single 25 kDa-immunoreactive band was observed which is identical to the band corresponding to the kappa L-chain as shown by western blot with the anti-mouse kappa chain antibody. Under-non-reducing SDS-PAGE followed by western blot with both the anti-kappa and the anti-Fab antibodies, mAb 4C5 was shown to migrate at approximately 50 kDa, and not at 150 kDa as a conventional IgG1 molecule. No mAb 4C5 immunoreactivity was detected after electrophoresis under both reducing and non-reducing conditions followed by western blot with an anti-Fcγantibody.

FIG. 3 A is a Coomasie stained SDS-PAGE of purified antibodies under reducing conditions. SDS-PAGE electrophoresis of purified antibodies under reducing conditions followed by Coomasie Brilliant Blue-R staining revealed in all cases, an approximately 25 kDa band corresponding to the L-chain.

FIG. 4A is a western blot of MDAMB453 lysates probed with a commercially available polyclonal anti-HSP90α antibody, mAb 4C5, recombinant and chimeric 4C5. In all cases a single 90 kDa immunoreactive band corresponding to HSP90 was observed. FIG. 4B is an immunoblot of anti-HSP90 immunoprecipitants of MDAMB453 lysates probed with mAb 4C5, recombinant 4C5, and chimeric 4C5. MDAMB453 cell lysates were immunoprecipitated with anti-HSP90 and immunoblotted with mAb 4C5, recombinant 4C5, and chimeric 4C5. In all cases a single immunoreactive band was observed. FIG. 4C is an immunoblot of mAb 4C5, recombinant 4C5, and chimeric 4C5 immunoprecipitants of MDAMB453 lysates probed with anti-HSP90α. Reverse immunoprecipitation experiments in MDAMB453 cell lysates were performed using mAb 4C5, rec 4C5 and ch 4C5, followed by Western blot with anti-HSP90α. In all cases a single immunoreactive band was observed indicating that both recombinant and chimeric 4C5 retain mAb 4C5 specificity and recognize HSP90.

FIGS. 5 A, 5B, 5C, and 5D show that recombinant and chimeric 4C5 bind to the cell surface and are not internalized by MDAMB453 cells.

FIG. 6 A is a panel of photomicrographs of the results of an in vitro wound healing assay. Photographs represent phase-contrast images obtained at zero time (left panel) and at 48 hours (right panel) after scratch formation, showing MDAMB453 cell migration either in control cultures or cultures including anti-HSP90α, mAb 4C5, recombinant 4C5, or chimeric 4C5. Scale bar: 200 μm. FIG. 6B is a graphical presentation of the wound healing assay results. Addition of 200 μg/ml of anti-HSP90α and mAb 4C5 in the culture medium resulted in a 48.57% and 55.3% inhibition of wound closure, respectively when compared to control cultures that were considered as resulting in 100% wound closure. Addition of 200 μg/ml recombinant 4C5 or chimeric 4C5 in the culture medium resulted in a 46.51% and 51.19% inhibition of wound closure, respectively. The bars represent the average of three independent experiments±SEM. Within a single experiment, each condition was tested in triplicate. Statistical significance of differences was tested by Student's T test. The presence of anti-HSP90α, mAb 4C5, recombinant 4C5, and chimeric 4C5 had a statistically significant effect on the wound closure (p<0.01, p<0.01, p<0.01 and p<0.01 respectively). FIG. 6C is a photomicrograph of phase-contrast images obtained at time zero (left panel) and at 24 hours after scratch formation (right panel), showing B16F10 melanoma cell invasion in a wound healing assay in the presence of 200 μg/ml of chimeric 4C5. Scale bar: 200 μm. FIG. 6D is a graphical presentation of the effect of increasing concentrations of chimeric 4C5 on the closure of the wound. Presence of 50 μg/ml chimeric 4C5 resulted in 16% inhibition of invasion, while addition of 100 μg/ml and 200 μg/ml chimeric 4C5 resulted in 27.9% and 52.3% inhibition of migration, respectively when compared to control cultures that were considered as resulting in 100% wound closure. FIG. 6E is a photomicrograph of dead cells visualized using Trypan Blue dye. Control, mAb 4C5-, anti-HSP90α-, and chimeric 4C5-treated cells were incubated with trypan blue in order to observe the rate of cell death in each case. Scale bar, 30 μm. FIG. 6F is a photomicrograph of control and chimeric 4C5 treated cells after being fixed, permeabilized, and stained with fluorescently labelled phalloidin. Scale bar 40 μm. FIG. 6G is a higher magnification showing phalloidin staining (F-actin). Chimeric 4C5 effectively blocks spreading of lamellipodia. Scale bar: 16 μm.

FIGS. 7 A and 7B show that chimeric 4C5 significantly reduced the number of cells in each individual colony formed by MDAMB231 human breast cancer cells in a clonogenic assay.

DETAILED DESCRIPTION OF THE INVENTION

Definitions

Figure 1A:
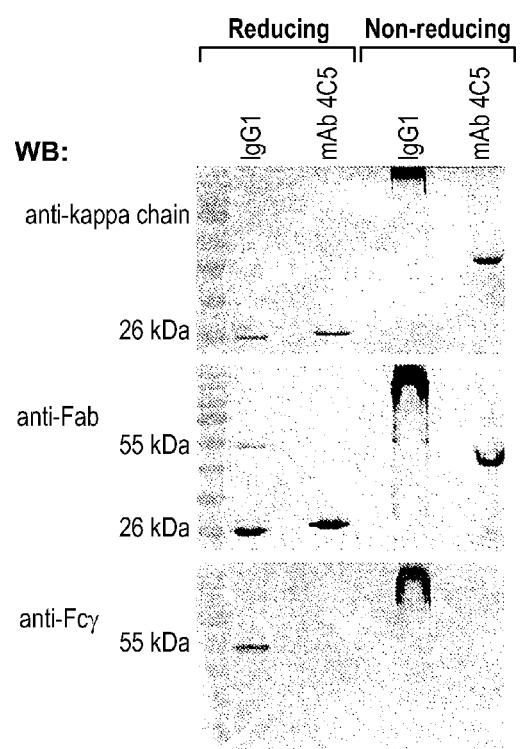
FIGS. 1 A and 1B show that mAb 4C5 is a kappa L-chain dimer that lacks heavy chains.
FIG. 1B is a Northern blot of 4C5 hybridoma RNA hybridized with a heavy chain probe. No radioactivity was detected after Northern blot analysis of 4C5 hybridoma-derived RNA with a heavy chain radiolabelled probe. 2D10- and NSO-derived RNA served as positive and negative control, respectively.

By "mAb 4C5" is meant a polypeptide having at least 75%, 85%, 90%, 95% or even 99% amino acid sequence identity to SEQ ID NO: 2, or a fragment thereof having antineoplastic activity and/or having HSP90-specific binding activity. mAb 4C5 is a murine antibody that specifically recognizes both the α and to a lesser extent the β isoforms of human heat shock protein 90 (HSP90).

The sequence of SEQ ID NO: 2 is provided below:

ELVMTQSPSSMYASLGERVTITCKASQDINSYLSWFQQKPGKSPKTLIYR

ANRLVDGVPSRFSGSGSGQDYSLTINSLEYEDMGIYYCLQYDEFPRLTFG

AGTRLELKRADAAPTVSIFPPSSEQLTSGGASVVCFLNNFYPKDINVKWK

IDGSERQNGVLNSWTDQDSKDSTYSMSSTLTLTKDEYERHNSYTCEATHK

TSTSPIVKS🟥🟥🟥NRNEC.

By "chimeric 4C5 protein" is meant a polypeptide having at least 75%, 85%, 90%, 95% or even 99% amino acid sequence identity to the amino acid sequence of SEQ ID NO: 4, or a fragment thereof having antineoplastic activity and/or having HSP90-specific binding activity. The human-mouse chimeric 4C5 antibody was constructed by replacing the mouse mAb 4C5 $C_K$ with the corresponding human $C_K$ domain. The human-mouse chimeric 4C5ΔCys protein was constructed by deleting the very last amino-acid (cysteine) of the human-mouse chimeric 4C5 antibody.

The sequence of SEQ ID NO: 4 is provided below:

ELVMTQSPSSMYASLGERVTITCKASQDINSYLSWFQQKPGKSPKTLIYR

ANRLVDGVPSRFSGSGSGQDYSLTINSLEYEDMGIYYCLQYDEFPRLTFG

AGTRLELKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGE🟥🟥🟥

By "chimeric 4C5 polynucleotide" is meant any nucleic acid molecule encoding a chimeric 4C5 polypeptide.

By "4C5 CDR1" is meant a polypeptide having at least 75%, 85%, 90%, 95% or even 99% amino acid sequence identity to SEQ ID NO: 5, wherein an antibody comprising 4C5 CDR1 has HSP90-specific binding activity. The sequence of SEQ ID NO: 5 is provided below:
KASQDINSYLS.

By "4C5 CDR2" is meant a polypeptide having at least 75%, 85%, 90%, 95% or even 99% amino acid sequence identity to SEQ ID NO: 6, wherein an antibody comprising 4C5 CDR2 has HSP90-specific binding activity. The sequence of SEQ ID NO: 6 is provided below:
RANRLVD.

By "4C5 CDR3" is meant a polypeptide having at least 75%, 85%, 90%, 95% or even 99% amino acid sequence identity to SEQ ID NO: 7, wherein an antibody comprising 4C5 CDR3 has HSP90-specific binding activity. The sequence of SEQ ID NO: 7 is provided below:
LQYDEFPRLT.

By "HSP90-specific binding activity" is meant that an antibody of the invention specifically binds to an HSP90 polypeptide.

By "ameliorate" is meant decrease, suppress, attenuate, diminish, arrest, or stabilize the development or progression of a disease. By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

In this disclosure, "comprises," "comprising," "containing" and "having" and the like can have the meaning ascribed to them in U.S. Patent law and can mean "includes," "including," and the like; "consisting essentially of or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "chimeric antibody" is meant an antibody comprising at least two discrete polypeptide fragments, a first polypeptide fragment from a murine antibody and a second polypeptide fragment from a human antibody. Each of the first and second polypeptide fragments are encoded by a nucleic acid construct and are operatively linked such that upon expression of the construct, a functional chimeric antibody comprising the murine antibody fragment linked to a human antibody fragment is generated. In one embodiment, the murine antibody fragment comprises one or more complementarity determining regions each of which specifically binds HSP90.

The term "cytotoxic moiety" includes, but is not limited to, abrin, ricin, *Pseudomonas* exotoxin, diphtheria toxin, botulinum toxin, or modified toxins thereof.

By "disease" is meant any condition or disorder that damages or interferes with the normal function of a cell, tissue, or organ. In one embodiment, the disease is a cancer or neoplasia.

By "effective amount" is meant the amount required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "fragment" is meant a portion of a polypeptide or nucleic acid molecule. This portion contains, in certain embodiments, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

By "functional moiety" is meant any compound, agent, molecule, etc., that possesses an activity or property that alters, enhances, or otherwise changes the ability of the targeting agent to fulfill any particular purpose or that enables the targeting agent to fulfill a new purpose. Such purposes include, but are not limited to, providing diagnostic and/or prognostic information and/or treatment of diseases or conditions associated with neoplasia.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. In certain embodiments, the preparation is at least 75%, at least 90%, and even at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any protein or polynucleotide having an alteration in expression level or activity that is associated with a disease or disorder.

By "neoplasia" is meant a disease characterized by the pathological proliferation of a cell or tissue and its subsequent migration to or invasion of other tissues or organs. Neoplasia growth is typically uncontrolled and progressive, and occurs under conditions that would not elicit, or would cause cessation of, multiplication of normal cells.

Neoplasias can affect a variety of cell types, tissues, or organs, including but not limited to an organ selected from the group consisting of bladder, bone, brain, breast, cartilage, glia, esophagus, fallopian tube, gallbladder, heart, intestines, kidney, liver, lung, lymph node, nervous tissue, ovaries, pancreas, prostate, skeletal muscle, skin, spinal cord, spleen, stomach, testes, thymus, thyroid, trachea, urogenital tract, ureter, urethra, uterus, and vagina, or a tissue or cell type thereof. Neoplasias include cancers, such as sarcomas, carcinomas, or plasmacytomas (malignant tumor of the plasma cells). In one embodiment, a neoplasia is breast cancer or melanoma.

Neoplasia cells that invade surrounding tissue or enter the bloodstream or lymphatic vessels form secondary tumors, or metastases, at a distance from the original tumor. Neoplasia that has metastasized is more difficult to treat and often has a poorer prognosis. Depending on the severity of the neoplasia (i.e., tumor size and invasiveness), a stage number is assigned, I, II, III, or IV. Stage I neoplasias are the least advanced and have the best prognosis. Stage II neoplasias typically include larger tumors and are associated with a somewhat poorer prognosis. Stage III and IV neoplasias have spread beyond their sites of origin and have the poorest prognosis.

As used herein, "obtaining" as in "obtaining an agent" includes synthesizing, purchasing, or otherwise acquiring the agent.

As used herein, "recombinant" includes reference to a polypeptide produced using cells that express a heterologous polynucleotide encoding the polypeptide. The cells produce the recombinant polypeptide because they have been genetically altered by the introduction of the appropriate isolated nucleic acid sequence. The term also includes reference to a cell, or nucleic acid, or vector, that has been modified by the introduction of a heterologous nucleic acid or the alteration of a native nucleic acid to a form not native to that cell, or that the cell is derived from a cell so modified. Thus, for example, recombinant cells express genes that are not found within the native (non-recombinant) form of the cell, express mutants of genes that are found within the native form, or express native genes that are otherwise abnormally expressed, under-expressed or not expressed at all.

By "reduces" is meant a negative alteration of at least 10%, 25%, 50%, 75%, or 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, at least about 20 amino acids, at least about 25 amino acids, and in certain embodiments, about 35 amino acids, about 50 amino acids, or about 100 amino acids. For nucleic acids, the length of the reference nucleic acid sequence will generally be at least about 50 nucleotides, at least about 60 nucleotides, at least about 75 nucleotides, and even about 100 nucleotides or about 300 nucleotides or any integer thereabout or there between.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1%) SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al, Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). In certain embodiments, such a sequence is at least 60%, 80% or 85%, 90%, 95% or even 99% identical at the amino acid level or nucleic acid to the sequence used for comparison (i.e., to a reference sequence). By "specifically binds" is meant a compound or antibody that recognizes and binds a polypeptide of the invention, but which does not substantially recognize and bind other molecules in a sample, for example, a biological sample, which naturally includes a polypeptide of the invention.

By "subject" is meant a mammal, including, but not limited to, a human or non-human mammal, such as a bovine, equine, canine, ovine, or feline.

A "tumor," as used herein, refers to all neoplastic cell growth and proliferation, whether malignant or benign, and all precancerous and cancerous cells and tissues.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof. Any compositions or methods provided herein can be combined with one or more of any of the other compositions and methods provided herein.

The invention provides polypeptides which possess anti-tumor properties. The polypeptides described herein include mouse-human chimeras corresponding to antibody light chains, that lack antibody heavy chains, yet retain the ability to bind to HSP90α protein.

The invention is based, at least in part, on the discovery that the monoclonal antibody 4C5 is completely devoid of a heavy chain and consists of a functional kappa light chain dimer, and the producing of recombinant chimeric mouse-human antibody light chain that retains the original antibody's specificity and functional properties. In particular, the chimeric antibody inhibited the function of surface HSP90 and reduced breast and melanoma cancer cell invasion in vitro, reduced the metastatic deposits and metastasis of triple-negative breast cancer cells into the lungs of SCID mice and delayed the primary tumor growth of MDAMB231 triple negative breast cancer cells growing orthotopically in SCID mice. These results indicate that this chimeric antibody is useful as an anti-cancer agent, with reduced adverse immunogenic effects.

Accordingly, the invention provides therapeutic compositions comprising mouse-human chimeric antibodies, and methods of using such antibodies to prevent, reduce, or eliminate the invasiveness of neoplastic cells (e.g., breast cancer and melanoma cells) or to otherwise treat a neoplasia or symptom thereof.

Antibodies

Antibodies (e.g., chimeric 4C5) that selectively bind an anti-HSP90 polypeptide are useful in the methods of the invention. Such antibodies are particularly useful for reducing or eliminating the growth and invasiveness of a neoplastic cell. In particular, such antibodies may be used to reduce or eliminate the development and metastatic potential of a tumor. As described herein below, binding to the HSP90 polypeptide reduces HSP90 biological activity in a neoplastic cell as assayed by analyzing the colony-forming ability and invasiveness of neoplastic cells. In some embodiments the colony-forming ability is tested by analyzing the growth of neoplastic cell colonies in vitro using a clonogenic assay. In certain embodiments, invasiveness is assayed in vitro by detecting migration of a neoplastic cell into a wound in culture, by detecting actin rearrangement, or by detecting the development of lamellipodia. In other embodiments, invasiveness is assayed by detecting the metastasis of a neoplastic cell in an animal model in vivo. Methods of preparing antibodies are well known to those of ordinary skill in the science of immunology. As used herein, the term "antibody" means not only intact antibody molecules, but also fragments of antibody molecules that retain immunogen-binding ability. Such fragments are also well known in the art and are regularly employed both in vitro and in vivo. Accordingly, as used herein, the term "antibody" means not only intact immunoglobulin molecules, but also the well-known active fragments F(ab')2, and Fab. F(ab')2, and Fab fragments that lack the Fc fragment of intact antibody, clear more rapidly from the circulation, and may have less non-specific tissue binding of an intact antibody (Wahl et al, J. Nucl. Med. 24:316-325 (1983). In certain embodiments, the antibodies of the invention comprise chimeric antibodies, humanized antibodies, fusion polypeptides, and unconventional antibodies. In other embodiments, the invention provides hybrid antibodies, in which one portion of the antibody is obtained from a first antibody (e.g., a murine antibody), while the other portion is obtained from a different second antibody (e.g., human antibody). Such antibodies are often referred to as "chimeric" antibodies. Such hybrids may also be formed using humanized antibodies.

In general, intact antibodies are said to contain "Fc" and "Fab" regions. The Fc regions are involved in complement activation and are not involved in antigen binding. An antibody from which the Fc region has been enzymatically cleaved, or which has been produced without the Fc region, designated an "$F(ab)_2$" fragment, retains both of the antigen binding sites of the intact antibody. Similarly, an antibody from which the Fc region has been enzymatically cleaved, or which has been produced without the Fc region, designated an "Fab" fragment, retains one of the antigen binding sites of the intact antibody. Fab fragments consist of a covalently bound antibody light chain and a portion of the antibody heavy chain, denoted "Fd." The Fd fragments are the major determinants of antibody specificity (a single Fd fragment may be associated with up to ten different light chains without altering antibody specificity). Isolated Fd fragments retain the ability to specifically bind to immunogenic epitopes.

Antibodies can be made by any of the methods known in the art utilizing HSP90, or immunogenic fragments thereof, as an immunogen. One method of obtaining antibodies is to immunize suitable host animals with an immunogen and to follow standard procedures for polyclonal or monoclonal antibody production. The immunogen will facilitate presentation of the immunogen on the cell surface. Immunization of a suitable host can be carried out in a number of ways. Nucleic acid sequences encoding a HSP90 polypeptide or immunogenic fragments thereof, can be provided to the host in a delivery vehicle that is taken up by immune cells of the host. The cells will in turn express the receptor on the cell surface generating an immunogenic response in the host. Alternatively, nucleic acid sequences encoding a HSP90 polypeptide, or immunogenic fragments thereof, can be expressed in cells in vitro, followed by isolation of the polypeptide and administration of the polypeptide to a suitable host in which antibodies are raised.

Alternatively, antibodies against a HSP90 polypeptide may, if desired, be derived from an antibody phage display library. A bacteriophage is capable of infecting and reproducing within bacteria, which can be engineered, when combined with human antibody genes, to display human antibody proteins. Phage display is the process by which the phage is made to 'display' the human antibody proteins on its surface. Genes from the human antibody gene libraries are inserted into a population of phage. Each phage carries the genes for a different antibody and thus displays a different antibody on its surface.

Antibodies made by any method known in the art can then be purified from the host. Antibody purification methods may include salt precipitation (for example, with ammonium sulfate), ion exchange chromatography (for example, on a cationic or anionic exchange column run at neutral pH and eluted with step gradients of increasing ionic strength), gel filtration chromatography (including gel filtration HPLC), and chromatography on affinity resins such as protein A, protein G, hydroxyapatite, and antiimmunoglobulin.

Antibodies can be conveniently produced from hybridoma cells engineered to express the antibody. Methods of making hybridomas are well known in the art. The hybridoma cells can be cultured in a suitable medium, and spent medium can be used as an antibody source. Polynucleotides encoding the antibody of interest can in turn be obtained from the hybridoma that produces the antibody, and then the antibody may be produced synthetically or recombinantly from these DNA sequences. For the production of large amounts of antibody, it is generally more convenient to obtain an ascites fluid. The method of raising ascites generally comprises injecting hybridoma cells into an immunologically naive histocompatible or immunotolerant mammal, especially a mouse. The mammal may be primed for ascites production by prior administration of a suitable composition (e.g., Pristane).

Antibodies produced by methods of the invention can be "humanized" by methods known in the art. "Humanized" antibodies are antibodies in which at least part of the sequence has been altered from its initial form to render it more like human immunoglobulins. Techniques to humanize antibodies are particularly useful when non-human animal (e.g., murine) antibodies are generated. Examples of methods for humanizing a murine antibody are provided in U.S. Pat. Nos. 4,816,567, 5,530,101, 5,225,539, 5,585,089, 5,693,762 and 5,859,205. In one embodiment, the heavy chain and light chain C regions are replaced with human sequence. In another version, the CDR regions comprise amino acid sequences for recognition of an antigen of interest, while the variable framework regions have also been converted to human sequences. It is well established that non-CDR regions of a mammalian antibody may be replaced with corresponding regions of non-specific or hetero-specific antibodies while retaining the epitope specificity of the original antibody. This technique is useful for the development and use of humanized antibodies in which non-human CDRs are covalently joined to human FR and/or Fc/pFc' regions to produce a functional antibody. In a third version, variable regions are humanized by designing consensus sequences of human and mouse variable regions, and converting residues outside the CDRs that are different between the consensus sequences.

In one embodiment humanized antibodies are generated by operably linking nucleic acid sequences encoding the amino acids comprising the CDRs (SEQ ID NO: 5, SEQ ID NO: 6, and SEQ ID NO: 7) to nucleic acid sequences encoding human Frame work region sequences (FR1, FR2, and FR3).

In other embodiments, the invention provides "unconventional antibodies."

Unconventional antibodies include, but are not limited to, nanobodies, linear antibodies (Zapata et al, Protein Eng. 8(10): 1057-1062, 1995), single domain antibodies, single chain antibodies, and antibodies having multiple valencies (e.g., diabodies, tribodies, tetrabodies, and pentabodies). Nanobodies are the smallest fragments of naturally occurring heavy-chain antibodies that have evolved to be fully functional in the absence of a light chain. Nanobodies have the affinity and specificity of conventional antibodies although they are only half of the size of a single chain Fv fragment. The consequence of this unique structure, combined with their extreme stability and a high degree of homology with human antibody frameworks, is that nanobodies can bind therapeutic targets not accessible to conventional antibodies. Recombinant antibody fragments with multiple valencies provide high binding avidity and unique targeting specificity to cancer cells. These multimeric scFvs (e.g., diabodies, tetrabodies) offer an improvement over the parent antibody since small molecules of ~60-100 kDa in size provide faster blood clearance and rapid tissue uptake See Power et al., (Generation of recombinant multimeric antibody fragments for tumor diagnosis and therapy. Methods Mol Biol, 207, 335-50, 2003); and Wu et al. (Anti-carcinoembryonic antigen (CEA) diabody for rapid tumor targeting and imaging. Tumor Targeting, 4, 47-58, 1999).

Various techniques for making unconventional antibodies have been described.

Bispecific antibodies produced using leucine zippers are described by Kostelny et al. (J. Immunol. 148(5): 1547-1553, 1992). Diabody technology is described by Hollinger et al. (Proc. Natl. Acad. Sci. USA 90:6444-6448, 1993). Another strategy for making bispecific antibody fragments by the use of single-chain Fv (sFv) dimers is described by Gruber et al. (J. Immunol. 152:5368, 1994). Trispecific antibodies are described by Tutt et al. (J. Immunol. 147:60, 1991). Single chain Fv polypeptide antibodies include a covalently linked $V_H$:$V_L$ heterodimer which can be expressed from a nucleic acid including $V_H$- and $V_L$-encoding sequences either joined directly or joined by a peptide-encoding linker as described by Huston, et al. (Proc. Nat. Acad. Sci. USA, 85:5879-5883, 1988). See, also, U.S. Pat. Nos. 5,091,513, 5,132,405 and 4,956,778; and U.S. Patent Publication Nos. 20050196754 and 20050196754.

Antibodies of the invention are particularly useful for the treatment of neoplasias, including breast cancer and melanoma, or other tumors including but not limited to gioblastomas, lymphomas, colon cancer, non-small cell lung cancer etc. Accordingly, the present invention provides methods of treating neoplastic disease and/or disorders or symptoms thereof which comprise administering a therapeutically effective amount of a pharmaceutical composition comprising a chimeric antibody described herein to a subject (e.g., a mammal such as a human). Thus, one embodiment is a method of treating a subject suffering from or susceptible to a neoplastic disease or disorder or symptom thereof. The method includes the step of administering to the mammal a therapeutic amount (of an amount) of a compound herein sufficient to treat the disease or disorder or symptom thereof, under conditions such that the disease or disorder is treated. The methods herein include administering to the subject (including a subject identified as in need of such treatment) a therapeutically effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

The therapeutic methods of the invention (which include prophylactic treatment) in general comprise administration of a therapeutically effective amount of the chimeric antibodies delineated herein to a subject (e.g. animal, human) in need thereof, including a mammal, particularly a human. Such treatment will be suitably administered to subjects, particularly humans, suffering from, having, susceptible to, or at risk for metastasis in connection with a neoplastic disease. Determination of those subjects "at risk" can be made by any objective or subjective determination by a diagnostic test or opinion of a subject or health care provider (e.g., genetic test, enzyme or protein marker, Marker (as defined herein), family history, and the like).

In one embodiment, the invention provides a method of monitoring treatment progress. The method includes the step of determining a level of diagnostic marker (Marker) (e.g., any target delineated herein modulated by a compound herein, a protein or indicator thereof, etc.) or diagnostic measurement (e.g., screen, assay) in a subject suffering from or susceptible to a disorder or symptoms thereof associated with neoplasia, in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In certain embodiments, a second level of Marker in the subject is determined at a time point later than the determination of the first level, and the two levels are compared to monitor the course of disease or the efficacy of the therapy. In certain embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

Recombinant Polypeptide Expression

The invention provides antibodies (chimeric antibodies) of the invention that are useful for the treatment of neoplasias. In particular, the invention provides a human-mouse chimeric 4C5 antibody, which can be expressed recombinantly. Typically, recombinant polypeptides are produced by transformation of a suitable host cell with all or part of a polypeptide-encoding nucleic acid molecule or fragment thereof in a suitable expression vehicle.

Those skilled in the field of molecular biology will understand that any of a wide variety of expression systems may be used to provide the recombinant protein. The precise host cell used is not critical to the invention. A polypeptide of the invention may be produced in a prokaryotic host (e.g., *E. coli*) or in a eukaryotic host (e.g., *Saccharomyces cerevisiae*, insect cells, e.g., Sf21 cells, or mammalian cells, e.g., NIH 3T3, HeLa, or COS cells). Such cells are available from a wide range of sources (e.g., the American Type Culture Collection, Rockland, Md.; also, see, e.g., Ausubel et al, Current Protocol in Molecular Biology, New York: John Wiley and Sons, 1997). The method of transformation or transfection and the choice of expression vehicle will depend on the host system selected. Transformation and transfection methods are described, e.g., in Ausubel et al. (supra); expression vehicles may be chosen from those provided, e.g., in Cloning Vectors: A Laboratory Manual (P. H. Pouwels et al, 1985, Supp. 1987).

A variety of expression systems exist for the production of the polypeptides of the invention. Expression vectors useful for producing such polypeptides include, without limitation, chromosomal, episomal, and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof.

One particular bacterial expression system for polypeptide production is the *E. coli* pET expression system (e.g., pET-28) (Novagen, Inc., Madison, Wis.). According to this expression system, DNA encoding a polypeptide is inserted into a pET vector in an orientation designed to allow expression. Since the gene encoding such a polypeptide is under the control of the T7 regulatory signals, expression of the polypeptide is achieved by inducing the expression of T7 RNA polymerase in the host cell. This is typically achieved using host strains that express T7 RNA polymerase in response to IPTG induction. Once produced, recombinant polypeptide is then isolated according to standard methods known in the art, for example, those described herein.

Another bacterial expression system for polypeptide production is the pGEX expression system (Pharmacia). This system employs a GST gene fusion system that is designed for high-level expression of genes or gene fragments as fusion proteins with rapid purification and recovery of functional gene products. The protein of interest is fused to the carboxyl terminus of the glutathione S-transferase protein from *Schistosoma japonicum* and is readily purified from bacterial lysates by affinity chromatography using Glutathione Sepharose 4B. Fusion proteins can be recovered under mild conditions by elution with glutathione. Cleavage of the glutathione S-transferase domain from the fusion protein is facilitated by the presence of recognition sites for site-specific proteases upstream of this domain. For example, proteins expressed in pGEX-2T plasmids may be cleaved with thrombin; those expressed in pGEX-3× may be cleaved with factor Xa.

Alternatively, recombinant polypeptides of the invention are expressed in *Pichia pastoris*, a methylotrophic yeast. *Pichia* is capable of metabolizing methanol as the sole carbon source. The first step in the metabolism of methanol is the oxidation of methanol to formaldehyde by the enzyme, alcohol oxidase. Expression of this enzyme, which is coded for by the AOX1 gene is induced by methanol. The AOX1 promoter can be used for inducible polypeptide expression or the GAP promoter for constitutive expression of a gene of interest.

Once the recombinant polypeptide of the invention is expressed, it is isolated, for example, using affinity chromatography. In one example, an antibody (e.g., produced as described herein) raised against a polypeptide of the invention may be attached to a column and used to isolate the recombinant polypeptide. Lysis and fractionation of polypeptide-harboring cells prior to affinity chromatography may be performed by standard methods (see, e.g., Ausubel et al, supra). Alternatively, the polypeptide is isolated using a sequence tag, such as a hexahistidine tag, that binds to nickel column.

Once isolated, the recombinant protein can, if desired, be further purified, e.g., by high performance liquid chromatography (see, e.g., Fisher, Laboratory Techniques In Biochemistry and Molecular Biology, eds., Work and Burdon, Elsevier, 1980). Polypeptides of the invention, particularly short peptide fragments, can also be produced by chemical synthesis (e.g., by the methods described in Solid Phase Peptide Synthesis, 2nd ed., 1984 The Pierce Chemical Co., Rockford, 111). These general techniques of polypeptide expression and purification can also be used to produce and isolate useful peptide fragments or analogs (described herein).

Antibodies and Analogs Thereof

The invention further provides antibodies (e.g., human/mouse chimeric antibodies) or fragments thereof that are modified in ways that enhance or do not inhibit their ability to reduce the growth, proliferation, or survival of a neoplastic cell. In one embodiment, the invention provides methods for optimizing the amino acid sequence of the chimeric antibody or the nucleic acid sequence encoding the chimeric antibody by producing an alteration. Such changes may include certain mutations, deletions, insertions, or post-translational modifications. In one embodiment, the amino acid sequence is modified to enhance protease resistance. Accordingly, the invention further includes analogs of any naturally-occurring polypeptide of the invention. Analogs can differ from the naturally-occurring the polypeptide of the invention by amino acid sequence differences, by post-translational modifications, or by both. Analogs of the invention will generally exhibit at least 75%, 85%>, 90%, 95% or even 99% identity with all or part of a naturally-occurring amino, acid sequence of the invention. The length of sequence comparison is at least 10, 13, 15 amino acid residues, at least 25 amino acid residues, and more than 35 amino acid residues. Again, in an exemplary approach to determining the degree of identity, a BLAST program may be used, with a probability score between $e^{-3}$ and $e^{-100}$ indicating a closely related sequence. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring polypeptides of the invention by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, Molecular Cloning: A Laboratory Manual (2d ed.), CSH Press, 1989, or Ausubel et al, supra). Also included are cyclized peptides, molecules, and analogs which contain residues other than L-amino acids, e.g., D-amino acids or non-naturally occurring or synthetic amino acids, e.g., β or γ amino acids.

In addition to full-length polypeptides, the invention also includes fragments of any one of the polypeptides of the invention. As used herein, the term "a fragment" means at least 5, 10, 13, or 15 amino acids in length. In other embodiments a fragment is at least 20 contiguous amino acids, at least 30 contiguous amino acids, or at least 50 contiguous amino acids, and in other embodiments at least 60 to 80 or more contiguous amino acids. Fragments of the invention can be generated by methods known to those skilled in the art or may result from normal protein processing (e.g., removal of amino acids from the nascent polypeptide that are not required for biological activity or removal of amino acids by alternative mRNA splicing or alternative protein processing events).

Antibody analogs having a chemical structure designed to mimic antibody functional activity (e.g., anti-neoplastic activity, antigen binding activity) can be administered according to methods of the invention. Methods of analog design are well known in the art, and synthesis of analogs can be carried out according to such methods by modifying the chemical structures such that the resultant analogs exhibit the antineoplastic activity of SEQ ID NO:2 or a chimeric antibody comprising SEQ ID NO:4$_{[PC6]}$. In certain embodiments, the antibody analogs are relatively resistant to in vivo degradation, resulting in a more prolonged therapeutic effect upon administration.

Assays for measuring functional activity include, but are not limited to, those described in the Examples below.

Pharmaceutical Therapeutics

The invention chimeric antibodies that are useful for the treatment of neoplasia. In one particular embodiment, the chimeric antibodies of the invention are useful for preventing or reducing tumor growth and the propensity of a neoplastic cell to invade a surrounding tissue or to otherwise metastasize. For therapeutic uses, the antibodies disclosed herein may be administered systemically, for example, formulated in a pharmaceutically-acceptable buffer such as physiological saline. In certain embodiments, routes of administration include, for example, subcutaneous, intravenous, interperitoneally, intramuscular, or intradermal injections that provide continuous, sustained levels of the drug in the patient. Treatment of human patients or other animals will be carried out using a therapeutically effective amount of a therapeutic identified herein in a physiologically-acceptable carrier. Suitable carriers and their formulation are described, for example, in Remington's Pharmaceutical Sciences by E. W. Martin. The amount of the therapeutic agent to be administered varies depending upon the manner of administration, the age and body weight of the patient, and with the clinical symptoms of the neoplasia. Generally, amounts will be in the range of those used for other agents used in the treatment of other diseases associated with neoplasia, although in certain instances lower amounts will be needed because of the increased specificity of the compound.

Therapeutic Methods

Antibodies of the invention (e.g., murine and human-murine chimeric antibodies described herein) are useful for preventing or ameliorating neoplastic disease. In one therapeutic approach, an agent identified or described herein is administered to the site of a potential or actual disease-affected tissue or is administered systemically. The dosage of the administered agent depends on a number of factors, including the size and health of the individual patient. For any particular subject, the specific dosage regimes should be adjusted over time according to the individual need and the professional judgment of the person administering or supervising the administration of the compositions.

Formulation of Pharmaceutical Compositions

The administration of a compound for the treatment of neoplasia may be by any suitable means that results in a concentration of the therapeutic that, combined with other components, is effective in ameliorating, reducing, or stabilizing a neoplasia. The compound may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, or intraperitoneally) administration route. An advantageous method of administration is intravenous infusion. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Pharmaceutical compositions according to the invention may be formulated to release the antibody substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively, constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in contact with the thymus; (v) formulations that allow for convenient dosing, such that doses are administered, for example, once every one or two weeks; and (vi) formulations that neoplasia by using carriers or chemical derivatives to deliver the therapeutic agent to a particular cell type (e.g., neoplastic cell). For some applications, controlled release formulations obviate the need for frequent dosing during the day to sustain the plasma level at a therapeutic level.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the therapeutic is formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes.

Parenteral Compositions

The pharmaceutical composition may be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions for parenteral use may be provided in unit dosage forms (e.g., in single-dose ampoules), or in vials containing several doses and in which a suitable preservative may be added (see below). The composition may be in the form of a solution, a suspension, an emulsion, an infusion device, or a delivery device for implantation, or it may be presented as a dry powder to be reconstituted with water or another suitable vehicle before use. Apart from the active agent that reduces or ameliorates a neoplasia, the composition may include suitable parenterally acceptable carriers and/or excipients. The active therapeutic agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents.

As indicated above, the pharmaceutical compositions according to the invention may be in the form suitable for sterile injection. To prepare such a composition, the suitable therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

Controlled Release Parenteral Compositions

Controlled release parenteral compositions may be in form of aqueous suspensions, microspheres, microcapsules, magnetic microspheres, oil solutions, oil suspensions, or emulsions. Alternatively, the antibody may be incorporated in biocompatible carriers, liposomes, nanoparticles, implants, or infusion devices. Materials for use in the preparation of microspheres and/or microcapsules are, e.g., biodegradable/bioerodible polymers such as polygalactia poly-(isobutyl cyanoacrylate), poly(2-hydroxyethyl-L-glutam-nine) and, poly(lactic acid).

Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly(glycolic acid) or poly(ortho esters) or combinations thereof).

Solid Dosage Forms for Oral Use

Formulations for oral use include tablets containing the active ingredient(s) in a mixture with non-toxic pharmaceutically acceptable excipients. Such formulations are known to the skilled artisan. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug in a predetermined pattern (e.g., in order to achieve a controlled release formulation) or it may be adapted not to release the active drug until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material, such as, e.g., glyceryl monostearate or glyceryl distearate may be employed.

The solid tablet compositions may include a coating adapted to protect the composition from unwanted chemical changes, (e.g., chemical degradation prior to the release of the chimeric antibody). The coating may be applied on the solid dosage form in a similar manner as that described in Encyclopedia of Pharmaceutical Technology, supra.

Formulations for oral use may also be presented as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders and granulates may be prepared using the ingredients mentioned above under tablets and capsules in a conventional manner using, e.g., a mixer, a fluid bed apparatus or a spray drying equipment.

Controlled Release Oral Dosage Forms

Controlled release compositions for oral use may, e.g., be constructed to release the chimeric antibody therapeutic by controlling the dissolution and/or the diffusion of the active substance. Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

A controlled release composition containing one or more therapeutic compounds may also be in the form of a buoyant tablet or capsule (i.e., a tablet or capsule that, upon oral administration, floats on top of the gastric content for a certain period of time). A buoyant tablet formulation of the compound(s) can be prepared by granulating a mixture of the compound(s) with excipients and 20-75% w/w of hydrocolloids, such as hydroxyethylcellulose, hydroxypropylcellulose, or hydroxypropylmethylcellulose. The obtained granules can then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice.

Combination Therapies

Optionally, chimeric antibody therapeutics of the invention may be administered in combination with any other chemotherapeutic; such methods are known to the skilled artisan and described in Remington's Pharmaceutical Sciences by E. W. Martin.

Kits

The invention provides kits for the treatment or prevention of neoplasia. In one embodiment, the kit includes a therapeutic or prophylactic composition containing a therapeutically effective amount of a chimeric antibody in unit dosage form. In some embodiments, the kit comprises a sterile container which contains a therapeutic or prophylactic cellular composition; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired a chimeric antibody of the invention is provided together with instructions for administering the chimeric antibody to a subject having or at risk of developing cancer (e.g., melanoma, breast cancer). The instructions will generally include information about the use of the composition for the treatment or prevention of neoplasia. In other embodiments, the instructions include at least one of the following: description of the therapeutic agent; dosage schedule and administration for treatment or prevention of ischemia or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1

MAb 4C5 Lacks a Heavy Chain

The electrophoretic motility of mAb 4C5, which was isolated from hybridoma cultures, was studied under reducing and non-reducing SDS-PAGE. This analysis revealed that this murine monoclonal antibody is not a conventional IgG molecule. When purified mAb 4C5 was subjected to reducing SDS-PAGE, followed by immunoblotting with an anti-mouse Fab antibody, the typical 25 kDa and 50 kDa bands, corresponding to the antibody light (L-) and heavy (H-) chains respectively, of a conventional IgG antibody were not observed. Instead a single band of approximately 25 kDa was seen (FIG. 1A). Interestingly, an identical 25 kDa single band was obtained after immunoblotting with an anti-kappa L-chain antibody (FIG. 1A). Accordingly, after non-reducing electrophoresis followed by immunoblotting with both the above mentioned antibodies, mAb 4C5 was shown to be significantly smaller than a conventional IgG1 molecule since it migrated at approximately 50 kDa instead of 150 kDa (FIG. 1A). Finally, no immunoreactivity was detected after electrophoresis of mAb 4C5 under both reducing and non-reducing conditions, followed by western blot analysis using an anti-Fcγantibody (FIG. 1A). Taken together, these data indicated that mAb 4C5 either lacks a part of its H-chain, or that it is completely devoid of a H-chain.

Figure 1B:
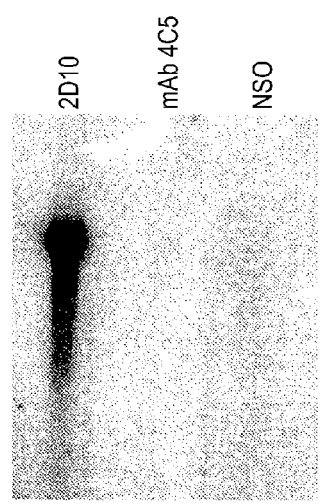

To further explore these possibilities, northern blot analysis as well as PCR amplification of the IgG1 H-chain cDNA was performed. In contrast to the positive control, no radioactivity was detected when RNAs derived from the mAb 4C5 hybridoma and NSO myeloma cells (negative control) were hybridized with the H-chain probe (FIG. 1B). These results indicated that mAb 4C5 likely completely lacks an H-chain gene. This was further confirmed by the H-chain PCR amplification experiments. For the amplification of the H-chain cDNA of mAb 4C5, a panel of 8 mouse universal primers and a polyA+ primer directed against the 5' and the 3' of the gene, respectively, were tested in several separate PCR reactions. In all conditions tested no amplification of a specific H-chain PCR product was observed. These combined data demonstrate that mAb 4C5 is devoid of an H-chain.

Example 2

A Human-mouse Chimeric Antibody was Constructed

Figure 2:
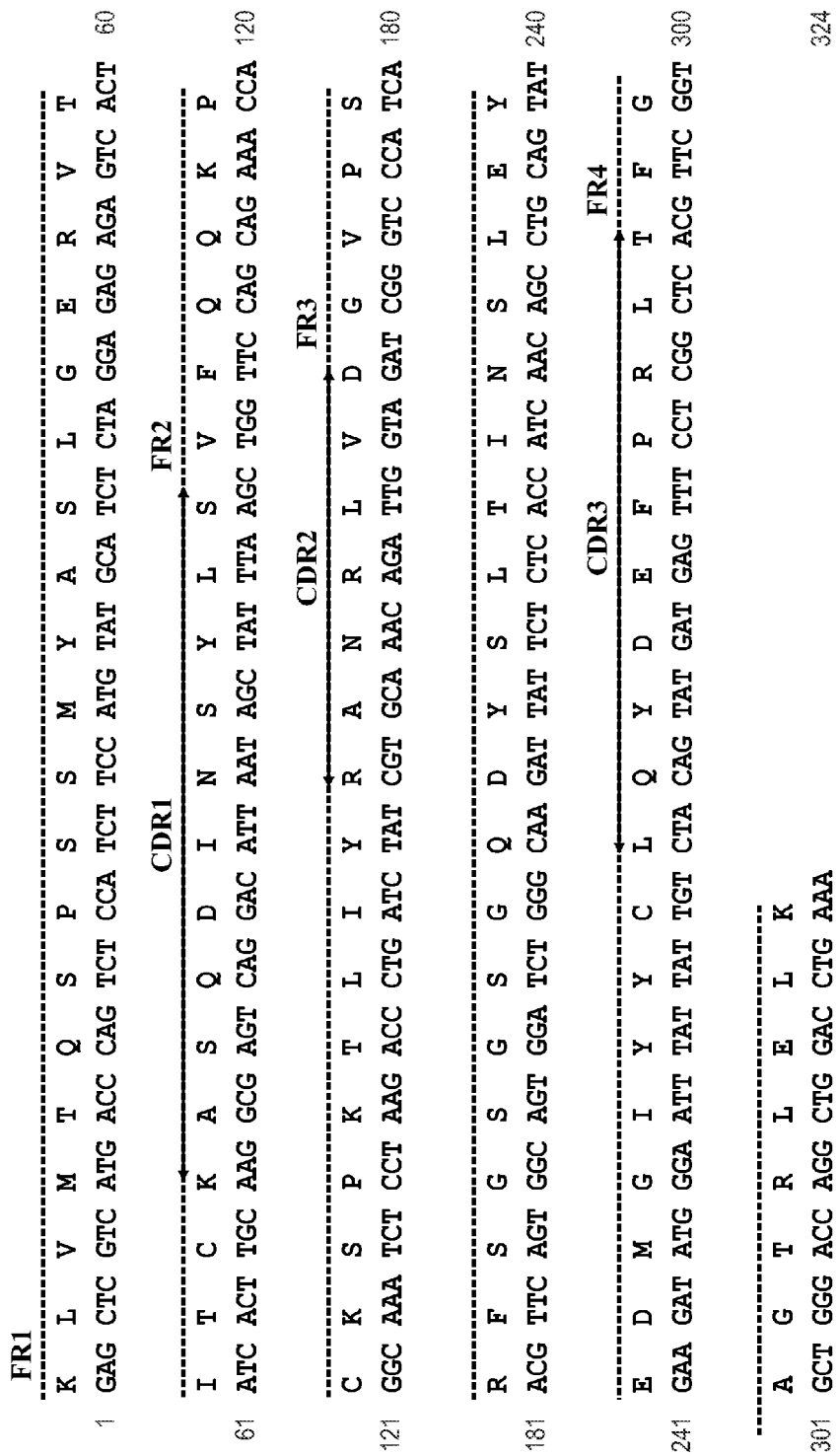
FIG. 2 shows the nucleotide (SEQ ID NO: 22) and deduced amino acid (SEQ ID NO: 23) sequences of mAb 4C5. The complementarity determining regions (CDRs) are underlined.

The cDNA encoding mAb 4C5 was isolated from 4C5 expressing hybridomas. The initial amplification of the mAb 4C5 kappa chain gene from the first strand cDNA template was performed using universal mouse L-chain primers. The approximately 650 by PCR product corresponding to the full length mAb 4C5 L-chain, was then subcloned into the SacI and XbaI restriction sites of the pComb3HSS$_{[PC7]}$ vector. The sequence analysis of cloned mAb 4C5 L-chain revealed that it belongs to the kappa chain subgroup I (FIG. 2).

Figure 3A:
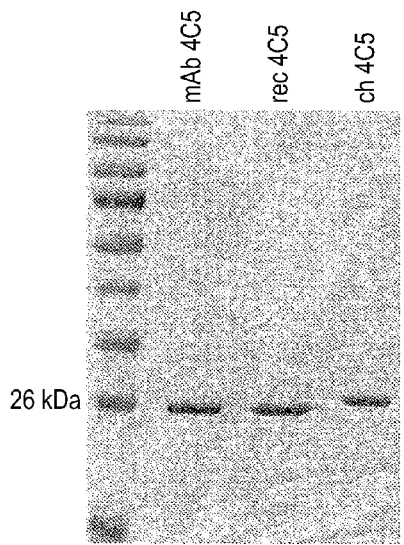
FIGS. 3 A and 3B show that both the mouse-human chimeric 4C5 and recombinant mouse 4C5 exhibit an electrophoretic mobility that is similar to that of the parental mAb 4C5.
FIG. 3B is a Coomasie stained SDS-PAGE of purified antibodies under non-reducing conditions. Under non-reducing conditions the antibodies are shown to migrate as a L-chain dimer. rec 4C5: recombinant 4C5, ch 4C5: chimeric 4C5.
FIG. 3C shows that monoclonal antibody ch4C5ΔCys is a monomer because it migrates around its predicted molecular weight of approximately 25 kDa in both reducing and non-reducing conditions$_{[PC1]}$.
Figure 3B:
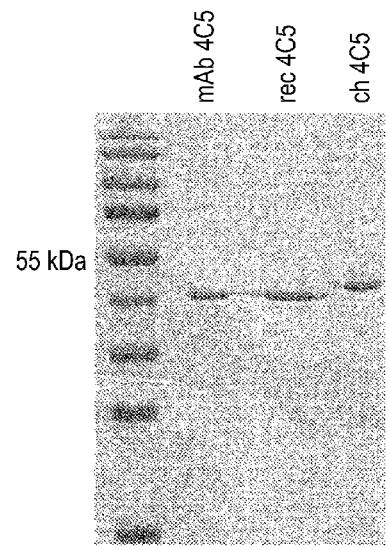

A human-mouse chimeric 4C5 antibody was constructed by replacing the mouse mAb 4C5 $C_K$ with the corresponding human $C_K$ domain. The sequence analysis of several recombinant clones confirmed the successful construction of the chimeric mouse-human 4C5. Both recombinant 4C5 and chimeric 4C5 antibodies were expressed in soluble forms in bacterial supernatants and purified. The electrophoretic motilities of the purified antibodies were tested with SDS-PAGE under reducing and non-reducing conditions and were found to be similar with the corresponding motility of the original mAb 4C5 antibody (FIG. 3).

To improve the translational efficacy of ch4C5 and in bacterial expression systems, standard molecular biology techniques known in the art were used to mutate the cDNA sequence of ch4C5 (SEQ ID NO: 3) at the wobble position, such as to remove rare tRNA codons (e.g., see Kane 1995:

Effects of rare codon clusters on high-level expression of heterologous proteins in *Escherichia coli*, Curr Opin Biotechnol. 1995 October; 6(5):494-500). SEQ ID NO: 9 exhibits a cDNA sequence of ch4C5 that is optimized for rare codon usage, leading to an improved yield in bacterial expression. Thus, ch4C5 can be expressed by usage of SEQ ID NO: 3, preferably by SEQ ID NO: 9. In addition, a chimeric 4C5 deletion mutant, referred to herein as ch4C5ΔCys, was constructed by removing the last three nucleotides of SEQ ID NO: 9, namely the triplet "TGC" encoding for cystein, to create SEQ ID: NO 10. Thus, ch4C5ΔCys can be expressed by usage of SEQ ID NO: 10 and the ch4C5ΔCys is identical to SEQ ID NO: 4 but for the last cysteine at the 3' end.

Figure 3C:
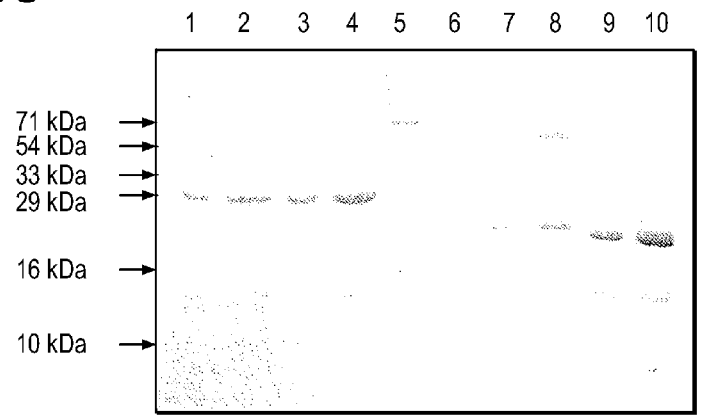

Purified chimeric 4C5 and ch4C5ΔCys antibodies expressed in bacteria as disclosed herein were analyzed with SDS-PAGE as shown in FIG. 3C: lanes 1-2 and 7-8: chimeric 4C5; lanes 3-4 and 9-10: ch4C5ΔCys; odd lanes correspond to 2 μg of loaded antibody, whereas even lanes to 5 μg, except from lanes 5 (molecular weight control and negative control, respectively). The monoclonal antibody ch4C5ΔCys migrated as a monomer under reducing or non-reducing conditions, suggesting that it exists predominantly as a monomer (FIG. 3C) Chimeric 4C5 migrated as a dimer under non-reducing conditions and as a monomer under reducing conditions, suggesting that it may exist as a monomer or as a dimer (FIG. 3C).

Example 3

Chimeric 4C5 Specifically Recognized HSP90

Figure 4A:
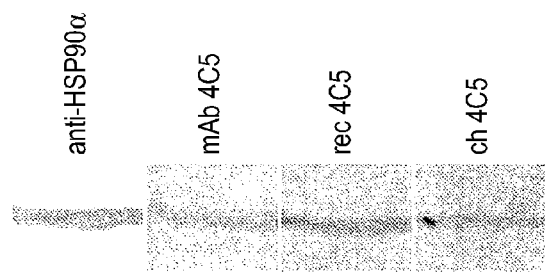
FIGS. 4A, 4B, and 4C show that recombinant and chimeric 4C5 specifically recognize HSP90.
Figure 4B:
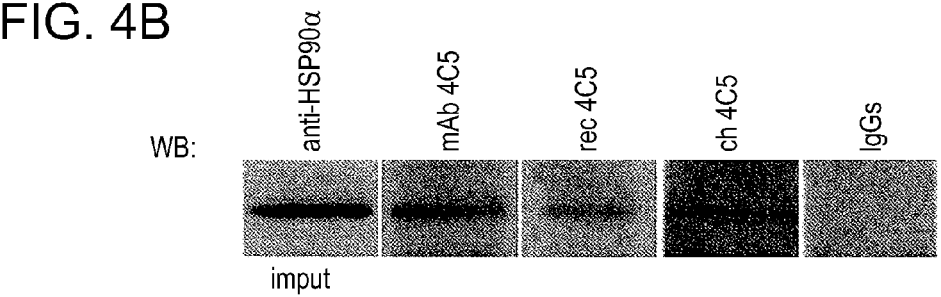
Figure 4C:
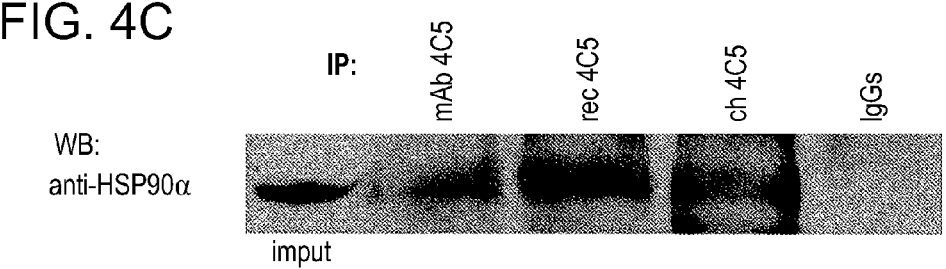

In order to explore the specificity of the recombinant L-chains, western blot analysis was performed in MDAMB453 breast cancer cell lysates using a commercially available polyclonal anti-HSP90α antibody (obtained from Chemicon), mAb 4C5, recombinant 4C5, and chimeric 4C5. In all cases a single identical immunoreactive band was observed (FIG. 4A), confirming that the mouse recombinant L-chain and the chimeric human-mouse L-chain retain the specificity of the paternal mAb 4C5. This was further confirmed by immunoprecipitation experiments performed in pre-cleared MDAMB453 cell lysates using polyclonal anti-HSP90 a followed by immunoblotting with mAb 4C5, recombinant 4C5, and chimeric 4C5. In all cases, a single immunoreactive band was observed, indicating that the chimeric light chain specifically recognized HSP90 (FIG. 4B). The same result was obtained when immunoprecipitation was performed using mAb 4C5, recombinant 4C5, and chimeric 4C5 followed by western blotting with the polyclonal anti-HSP90α antibody (FIG. 4C). In all experiments an irrelevant mouse IgG was used as a negative control.

Example 4

Figure 5A:
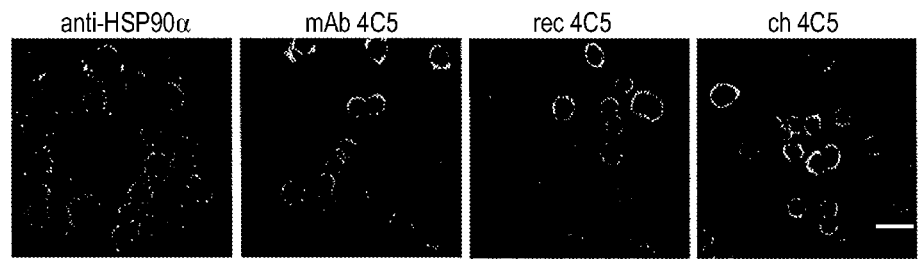
FIG. 5A is a photomicrograph of immunofluorescence staining of MDAMB453 cells using recombinant and chimeric 4C5. The punctuate immunolabeling indicates the surface pool of HSP90. Similar results were obtained using mAb 4C5 and anti-HSP90α. Negative controls were performed using an antibody against the intracellular protein βtubulin. (not shown) Scale bar: 20 μm.
Figure 5B:
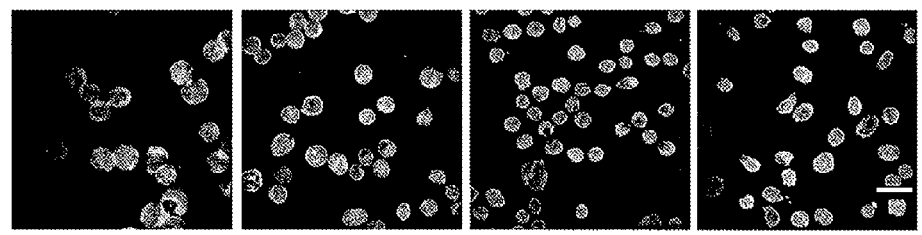
FIG. 5B is a photomicrograph of recombinant and chimeric 4C5 binding to intracellular HSP90. Similarly to the murine antibody the recombinant and chimeric 4C5 also recognize the intracellular pool of HSP90 following cell permeabilization. Immunofluoresence detection of intracellular HSP90 in MDAMB453 cells was performed under fixed conditions with 4% paraformaldeyde and permeabilization with 0.1% Triton X-100. Scale bar: 20 μm.
Figure 5C:
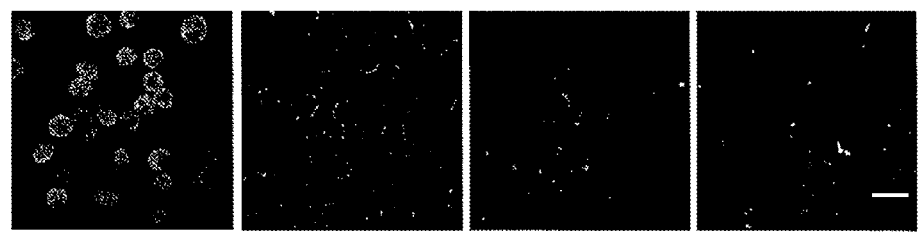
FIG. 5C is a photomicrograph of detection of antibody internalization. Cells were incubated at 37° C. with the antibodies for various time intervals, fixed, and permeabilized. Binding of the antibodies was visualized using a fluorescence-conjugated antibody. No internalization of the mAb 4C5, recombinant 4C5, and chimeric 4C5 antibodies was observed—even after 24 of incubation. In contrast, anti-HSP90α antibody was detected intracellularly after 8 hours of incubation. Scale bar: 20 μm.

A Human/mouse Chimeric Light Chain Antibody Bound to the Cell Surface and was not Internalized by MDAMB453 Cells Previous studies have shown that mAb 4C5 specifically binds to surface HSP90. In order to investigate whether the chimeric 4C5 antibody also retains this feature, unfixed MDAMB453 cultures were incubated with recombinant 4C5 and chimeric 4C5 L-chains, and after 2 hours in culture, the cells were carefully washed, fixed, and labelled with fluorescence-conjugated secondary antibody. Thus, the primary antibody had access only to the external surface of the cells. The observed typical punctuate immunostaining confirmed the cell surface localization of HSP90 (FIG. 5A). Similar results were obtained using commercial anti-HSP90α and of course mAb 4C5 (FIG. 5A). It is noteworthy that similarly to mAb 4C5, chimeric 4C5 as well as recombinant 4C5 also recognized the intracellular HSP90 as demonstrated by immunofluoresence after fixation and permeabilization of MDAMB453 cells (FIG. 5B). Finally, the binding of both L-chain antibodies to living MDAMB453, was monitored at various time intervals. After incubation with the antibodies at 37° C., cells were fixed, permeabilized, and stained with a fluorescence-conjugated secondary antibody. It was shown that like to mAb 4C5 and in contrast to anti-HSP90α, recombinant and chimeric 4C5 were not internalized, but remained bound on the cell surface (FIG. 5C).

Example 5

Chimeric Light Chain Did not Affect the Function of Intracellular HSP90

The significance of the cell impermeability of the chimeric L-chain antibody was investigated by monitoring the levels of certain HSP90 intracellular client proteins. To date more than one hundred intracellular HSP90 client proteins have been identified. Cell-permeable HSP90 inhibitors induce the degradation of these proteins because their stability depends on intracellular HSP90 function. Because data demonstrated that mAb 4C5, recombinant 4C5, and chimeric 4C5 are all likely to be cell impermeable, their ability to affect the stability of three well-characterized intracellular HSP90 client proteins (Akt, cRaf, and ErbB2) was examined.

Figure 5D:
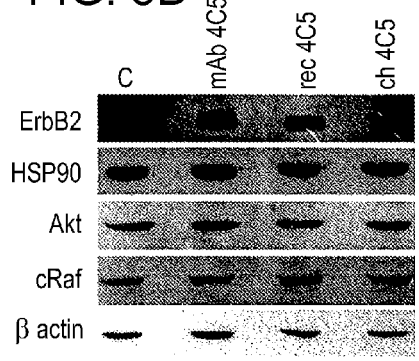
FIG. 5D is a western blot of cell lysates derived from MDAMB453 cells treated with mAb 4C5, recombinant 4C5, or chimeric 4C5 probed with antibodies against ErbB2, Akt, cRaf, and HSP90. Actin served as a loading control. Treatment with the three 4C5 antibodies did not affect the levels of the intracellular kinases tested as compared to controls.

MDAMB453 breast cancer cells were incubated with the indicated concentrations of either mAb 4C5, recombinant 4C5, or chimeric 4C5 followed by monitoring of Akt, cRaf, and ErbB2 levels by western blotting. As shown in FIG. 5D the antibodies tested did not affect the steady-state levels of any of the HSP90 client proteins.

Example 6

Figure 6A:
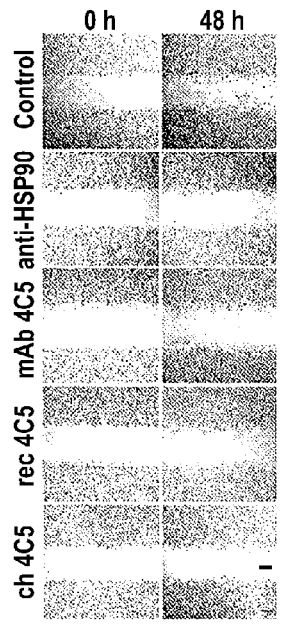
FIGS. 6A, 6B, 6C, 6D, 6E, 6F, and 6G show that both recombinant and chimeric 4C5 retain the function blocking properties of mAb 4C5 and inhibit MDAMB453 breast cancer and B16F10 melanoma cell invasion.
Figure 6B:
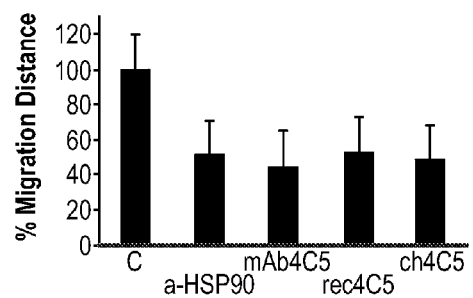
Figure 6C:
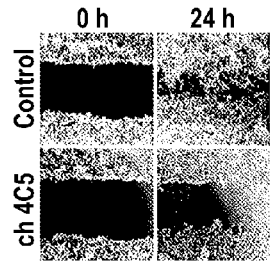
Figure 6D:
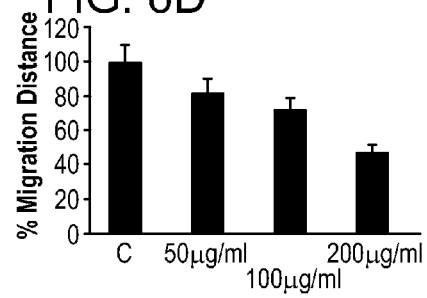

Chimeric Light Chain Antibody Inhibited MDAMB453 and B16 F10 Cancer Cell Invasion in a Wound Healing Assay Previous studies have shown that mAb 4C5 inhibits MDAMB453 breast cancer and B 16 F10 melanoma cell invasion in a wound healing assay. In order to determine whether the chimeric antibody exhibited the same functional property as the parental mAb 4C5, in vitro wound healing assays were performed using MDAMB453 and B16 F10 cancer cells. As shown in FIGS. 6A and 6B, the presence of chimeric 4C5 in the culture medium significantly reduced the rate of MDAMB453 cancer cell invasion within the migration gap after 48 hours, as compared to control cultures. The inhibition rate of MDAB453 invasion was similar to that obtained when the anti-HSP90α, as well as the parental mAb 4C5 and the recombinant 4C5 were included in the culture medium (FIGS. 6A and B). Similar results were obtained in a wound healing assay using B 16 F10 melanoma cells and increasing concentrations of chimeric 4C5 (FIGS. 6C and 6D). Interestingly, the inhibition of melanoma cell invasion was dose dependent indicating the specificity of the antibody (FIG. 6D). Control cultures were grown either in culture medium alone, or in culture medium containing 200 μg/ml of an irrelevant IgG1 antibody. It is important to note that no statistically significant difference was observed between the two types of controls used. The control value illustrated is the mean value of the two types of control.

Figure 6E:
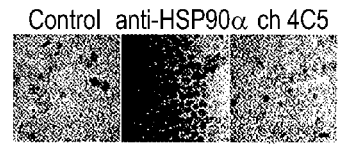

It should be noted that the inhibitory effect of the anti-HSP90α antibody on the invasion rate of the MDAMB453 cells was at least in great part due to the increased cell death as judged by trypan blue staining (FIG. 6E). In contrast, when cultures were treated with mAb 4C5 and chimeric 4C5, the cell death rate was similar to that observed in the control cultures (FIG. 6E). This result further supports that the chimeric 4C5, in contrast to the polyclonal anti-HSP90αantibody, is not internalized and thus does not affect the intracellular pool of HSP90 which is important for cell survival.

Figure 6F:
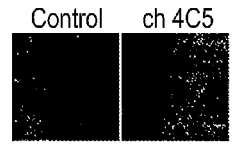
Figure 6G:

The above described cultures were examined with respect to actin re-arrangement dynamics using fluorescently labelled phalloidin. When cultures were exposed to the chimeric L-chain, less cell spreading was observed as compared to control cultures, and a morphology indicative of non-motile cells was seen. Furthermore, when these cultures were visualized at a higher magnification, lamellipodia were less developed and spread out as compared to lamellipodia of MDAMB453 in control cultures (FIGS. 6F and 6G). These results are in accordance to previously published data regarding the effect of mAb 4C5 on actin re-arrangement and lamellipodia development.

Figure 6H:
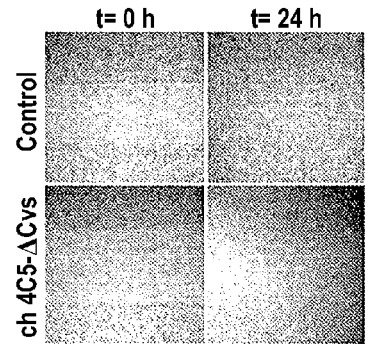
FIG. 6H shows that ch4C5ΔCys inhibits B16F10 mouse melanoma cell migration in an in vitro wound healing assay. Photographs represent phase-contrast images obtained at zero time (left panel) and at 24 hours (right panel) after scratch formation, showing B16F10 mouse melanoma cell migration either in control cultures or cultures including ch4C5ΔCys$_{[PC2]}$.
Figure 7A:
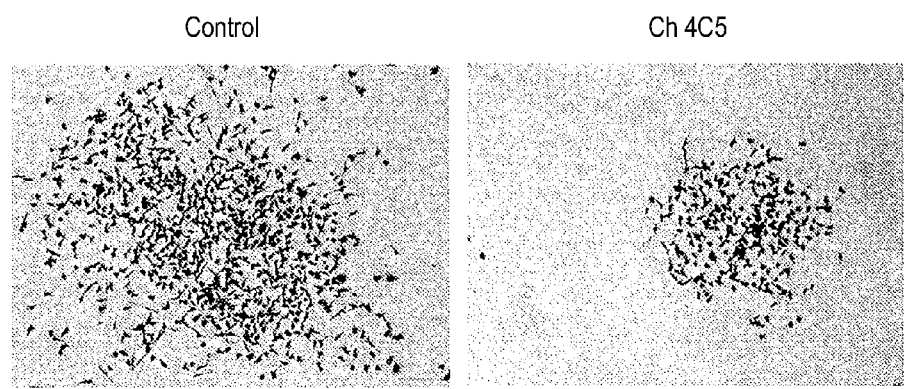
FIG. 7A is a photomicrograph of the results of the colony formation assay showing Giemsa stained colonies of MDAMB231 cells either in control or in chimera 4C5 treated cultures.
Figure 7B:
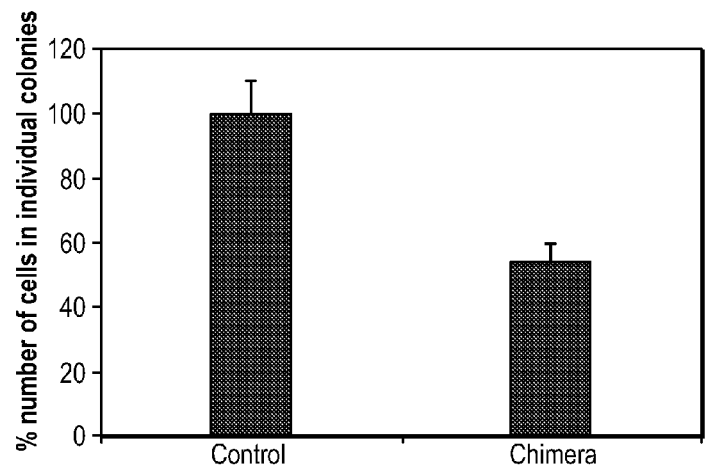
FIG. 7B is a graphical presentation of the effect of the chimera 4C5 on the number of cells in each colony. A 47.3% reduction is observed (p<0.001) when compared to control cultures.
Figure 8A:
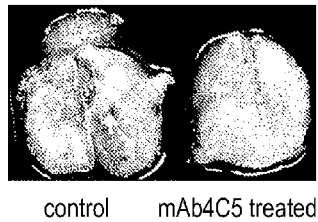
FIG. 8 shows that monoclonal Ab 4C5 inhibits the metastatic deposition of breast cancer$_{[PC3]}$ cells into the lungs of SCID mice.
Figure 8B:
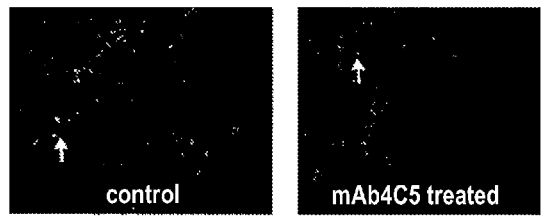
Figure 8C:
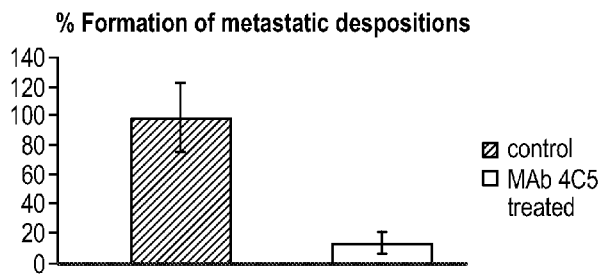
Figure 8D:
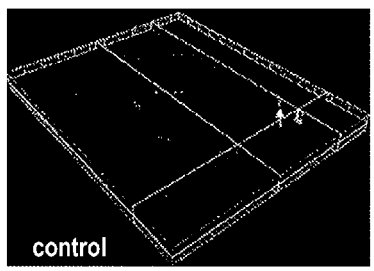
Figure 8E:
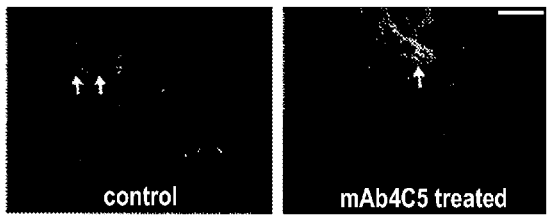
Figure 8F:
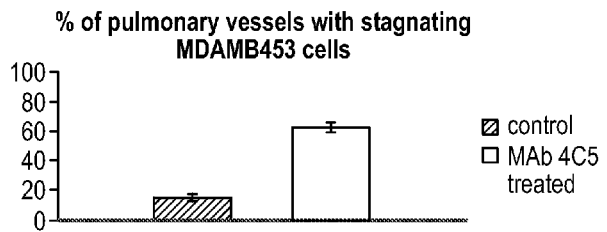

Finally, FIG. 6H shows that ch4C5ΔCys inhibits B16F10 mouse melanoma cell migration in an in vitro wound healing assay. Photographs represent phase-contrast images obtained at zero time (left panel) and at 24 hours (right panel) after scratch formation, showing B16F10 mouse melanoma cell migration either in control cultures or cultures including ch4C5ΔCys$_{[PC8]}$.

Example 7

Chimeric Light Chain Antibody Significantly Reduced the Number of Cells in Each Individual Colony Formed by MDAMB231 Human Breast Cancer Cells in a Clonogenic Assay In order to investigate the capacity of the chimera 4C5 to affect the capacity of MDAMB231 human breast cancer cells to form colonies a clonogenic assay was performed. When cultures were exposed to the chimeric L-chain a significant reduction of the number of cells in each individual colony was observed when compared to control cultures. This result indicates that the chimeric antibody has a cytostatic effect on the development of human breast cancer colonies.

The experiments reported herein describe the cloning and sequencing of an anti-HSP90 murine monoclonal antibody, named mAb 4C5. More importantly, it was found that mAb 4C5 is not a conventional IgG molecule, but instead is completely devoid of a H-chain and consists of a κ light chain dimer. This was initially supported by SDS-PAGE electrophoresis under denaturing and non-denaturing conditions, demonstrating that mAb 4C5 migrated unconventionally at approximately 26- and 50-kDa, respectively. Additionally, when total RNA isolated from the mAb 4C5-producing hybridoma cell line was subjected to northern blot hybridization using an IgG1 H-chain cDNA radio-labeled probe, no radioactivity could be detected. In agreement with the above results, the H-chain cDNA could not be amplified using universal mouse H-chain primers. Finally, the extra-ordinary nature of mAb 4C5 was confirmed beyond any doubt, since the recombinant κ light chain expressed in bacteria was shown to retain all the properties of the paternal antibody, including antigen binding and in vitro inhibition of cancer cell invasion.

This monoclonal antibody was originally produced by immunization of mice with a brain membrane fraction of 15-day-old rat embryos (Thomaidou D, Patsavoudi E. Identification of a novel neuron-specific surface antigen in the developing nervous system, by monoclonal antibody 4C5. Neuroscience. 1993; 53: 813-27), and it was shown to specifically recognize and inhibit the function of surface HSP90 during cell migration processes (Sidera K, Samiotaki M, Yfanti E, Panayotou G, Patsavoudi E.

Involvement of cell surface HSP90 in cell migration reveals a novel role in the developing nervous system. J Biol. Chem. 2004; 279: 45379-88). Additionally, mAb 4C5 was shown to significantly reduce the rate of invasion and metastasis of cancer cells. More specifically, it was demonstrated that this antibody inhibits melanoma cell invasion and metastasis (Stellas D, Karameris A, Patsavoudi E. Monoclonal antibody 4C5 immunostains human melanomas and inhibits melanoma cell invasion and metastasis. Clin Cancer Res. 2007; 13: 1831-8) as well as the interaction of surface HSP90 with the extracellular domain of HER-2, leading to impaired downstream signalling and subsequently reduced rate of in vitro breast cancer cell invasion (Sidera K, Gaitanou M, Stellas D, Matsas R, Patsavoudi E. A critical role for HSP90 in cancer cell invasion involves interaction with the extracellular domain of HER-2. J Biol. Chem. 2008; 283: 2031-41).

It is well known that murine antibodies have limited use for in vivo therapy in humans because of their immunogenicity. This problem has been overcome using genetic engineering approaches to produce chimeric mouse-human and fully human antibodies. Taking into consideration the unconventional nature of mAb 4C5 in combination with the fact that during the humanization process the antibody affinity is frequently reduced, the murine mAb was reconstituted into a functional mouse-human chimeric version that, similarly to the paternal antibody binds to surface HSP90 and inhibits cancer cell invasion. The chimeric antibody which was engineered by replacing the C-region of the paternal murine antibody with the corresponding human C-region, was shown to retain the specificity and affinity of the paternal mouse antibody.

It has been a generally accepted conception that the antibody molecule requires both the H- and L-chains for its full activity (Sastry L, Alting-Mees M, Huse W D, Short J M, Sorge J A, Hay B N, et al. Cloning of the immunological repertoire in *Escherichia coli* for generation of monoclonal catalytic antibodies: construction of a heavy chain variable region-specific cDNA library. Proc Natl Acad Sci USA. 1989; 86: 5728-32).

Moreover, the H-chain is believed to be the predominant contributor to the free energy of binding while the contribution of the L-chain to antigen binding is supposed to be limited (Novotny J, Bruccoleri R E, Saul F A. On the attribution of binding energy in antigen-antibody complexes McPC 603, D1.3, and HyHEL-5. Biochemistry. 1989; 28: 4735-49; Ward E S, Gussow D, Griffiths A D, Jones P T, Winter G. Binding activities of a repertoire of single immunoglobulin variable domains secreted from *Escherichia coli*. Nature. 1989; 341: 544-6). The latter is further supported by the fact that cameloids possesses a class of fully functional antibodies completely lacking L-chains and consisting of H-chain dimers (Hamers-Casterman C, Atarhouch T, Muyldermans S, Robinson G, Hamers C, Songa E B, et al. Naturally occurring antibodies devoid of light chains. Nature. 1993; 363: 446-8;

Muyldermans S, Cambillau C, Wyns L. Recognition of antigens by single-domain antibody fragments: the superfluous luxury of paired domains. Trends Biochem Sci. 2001; 26: 230-5). In context to these findings, H-chains alone were shown to interact with a variety of antigens in a specific manner (albeit with lower affinity than the intact antibodies), which has led to the use of single domain antibodies derived from the H-chains (Winter G, Milstein C. Man-made antibodies. Nature. 1991; 349: 293-9).

In the past, antigen binding by L-chains has been sporadically demonstrated. The first reports of free immunoglobulin light chains concerned the so called Bence-Jones proteins. These were reported as L-chain dimers expressed by multiple myeloma cells, collected from the urine of human patients (Bradwell A R, Carr-Smith H D, Mead G P, Harvey T C, Drayson M T. Serum test for assessment of patients with Bence Jones myeloma. Lancet. 2003; 361: 489-91). Furthermore, large amounts of L-chains accumulate in the extracellular fluids and tissues of patients with L-chain secreting tumors (Stevens F J, Solomon A, Schiffer M. Bence Jones proteins: a powerful tool for the fundamental study of protein chemistry and pathophysiology. Biochemistry. 1991; 30: 6803-5). In 1993 Mei Sun et al., (Sun M, Li L, Gao Q S. Paul S. Antigen recognition by an antibody light chain. J Biol. Chem. 1994; 269: 734-8) reported that a purified L-chain from a monoclonal antibody against vasoactive intestinal polypeptide (VIP) displayed sequence-specific and high affinity binding to VIP. Accordingly, Nishimura E et al., (Nishimura E, Mochizuki K, Kato M, Hashizume S, Haruta H, Shirahata S, et al. Recombinant light chain of human monoclonal antibody HB4C5 as a potentially useful lung cancer-targeting vehicle. Hum Antibodies. 1999; 9: 1 11-24) reported the recombinant production of a λ light chain exhibiting a significantly higher activity of binding to the antigen as compared with the intact antibody. Furthermore, the authors presented evidence that this recombinant light chain could serve as a potentially useful vehicle for clinical use such as radioimmunoimaging and radioimmunotherapy of lung cancers. It has been also reported that antibody L-chain dimers produced by a mouse hybridoma reacted to human melanoma tissues (Masat L, Wabl M Johnson J P. A simpler sort of antibody. Proc Natl Acad Sci USA. 1994; 91: 893-6). In 1998 Pereira B et al, (Pereira B, Benedict C R, Le A, Shapiro S S, Thiagarajan P. Cardiolipin binding a light chain from lupus-prone mice. Biochemistry. 1998; 37: 1430-7) showed that a single L-chain variable sequence contains all the determinants necessary for cardiolipin binding, with an affinity similar to that of the intact antibody. More recently, Dubnovitsky A P et al, (Dubnovitsky A P, Kravchuk Z I, Chumanevich A A, Cozzi A, Arosio P, Martsev S P. Expression, refolding, and ferritin-binding activity of the isolated $V_L$-domain of monoclonal antibody F1 1. Biochemistry (Mosc). 2000; 65: 1011-8) reported that the recombinant $V_L$-domain of a monoclonal antibody against ferritin preserved its antigen binding function and that the antigen binding constant of the $V_L$-domain is comparable to that of the full-length parental antibody.

The results reported herein represent the first experimental evidence of a L-chain dimer having a function-blocking activity. More specifically, the present work demonstrated that both the recombinant and chimeric 4C5 consisting of an L-chain dimer have a high specific activity as examined by immunoblotting and immunofluoresence experiments using breast cancer cells. Furthermore and similarly to the paternal antibody they exhibit function-blocking properties as judged by the in vitro wound healing assay. These results provide a new understanding for comprehensive approaches in the clinical applications of L-chain antibodies. Recombinant L-chain antibodies have a number of advantages over usual antibodies and VH antibodies when intended for human therapeutics, i.e., easy and reproducible production with constant quality, higher solubility and resistance to aggregation, faster clearance from circulation, among others. Especially in the case of mAb 4C5, two additional attributes make its chimerization valuable for therapeutic use. First, its ability to functionally inhibit specifically the HSP90 pool localized on the cell surface without interfering with HSP90 functions inside the cell; and secondly, its minimal immunogenicity in a clinical setting due to its largely human composition. Therefore, the development of chimeric Ab 4C5 represents an important step in the development of novel HSP90 inhibitors for the treatment of human malignancies.

Example 8

Monoclonal Ab 4C5 Inhibits the Metastatic Deposition of Breast Cancer Cells into the Lungs of SCID Mice[PC9]

To explore the inhibitory effects of mAb 4C5 against the metastatic behavior of malignant breast cancer cells in vivo, MDAMB453 breast cancer cells labeled with the fluorescent dye DiI were injected intravenously in SCID mice, either in the presence or in the absence of 100 µg/ml of mAb 4C5. Twenty four hours after the injection, mice were euthanized and the metastatic deposits of cells were traced and evaluated in the lungs of both the control and the mAb 4C5 treated groups.

FIG. 8 shows that mAb 4C5 inhibits the metastatic deposition of breast cancer cells into the lungs of SCID mice. At the macroscopic level an important number of metastatic cell deposits (arrow in FIG. 8A) was observed in control animals as compared to mAb 4C5 treated mice. This was confirmed microscopically where a very important decrease in the deposition of cancer cells was detected in the mAb 4C5 treated mice (arrows in FIG. 8B). Quantification of the metastatic deposit formation revealed a 86.67% inhibition in the mAb 4C5 treated mice when compared with control mice (FIG. 8C). In order to further visualize the deposition of MDAMB453 cells in the lung tissue, we performed a 3D reconstitution of a cryosection derived from a control animal where the infiltration of metastatic deposits of MDAMB453 cells in the lung tissue is clearly demonstrated (arrow in FIG. 8D). It is of interest to note that in the mAb 4C5 treated mice, MDAMB453 cells were often observed stagnating on the inner surface of large pulmonary blood vessels whereas no such images could be detected in the control animals (arrows in FIG. 8E). Quantification of this occurrence revealed that in 58.76% of the pulmonary vessels visualized in the, mAb4C5 treated animals, MDAMB453 cells were observed stagnating on the inner surface of the vessels. In contrast, only 15.4% of the vessels observed in the control animals showed intravascular retention of the cancer cells (FIG. 8F) These results demonstrate that mAb 4C5 inhibits the metastatic deposition of MDAMB453 cancer cells into the lungs of SCID mice.

Example 9

Figure 9:
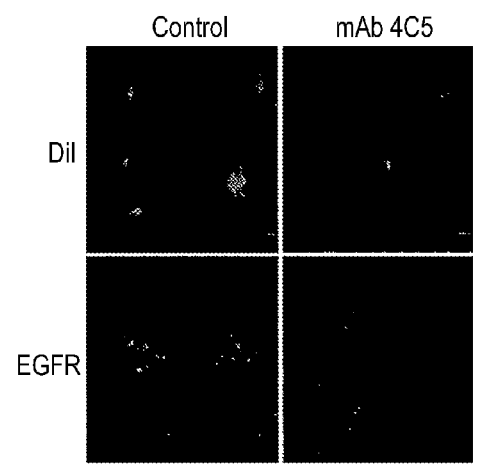
FIG. 9 shows that monoclonal Ab 4C5 inhibits the metastasis of triple-negative breast cancer cells into the lungs of SCID mice.
Figure 9:
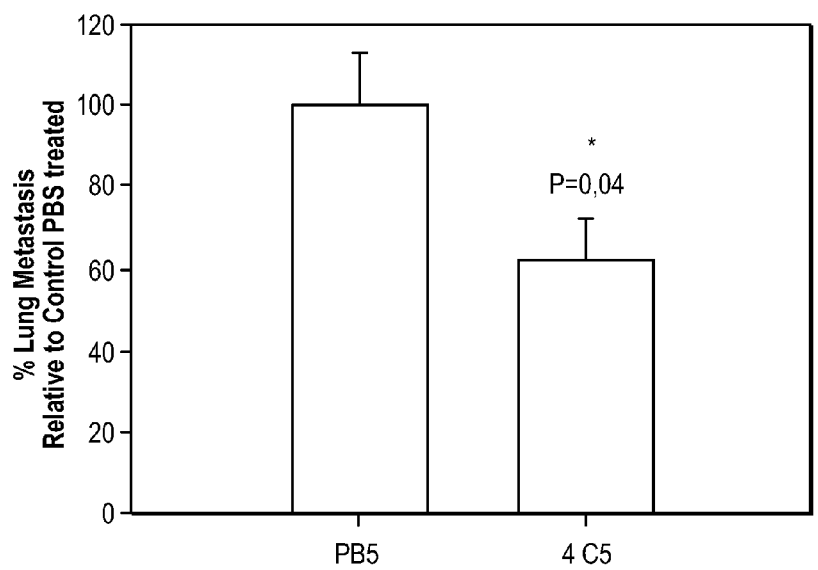

Monoclonal Ab 4C5 Inhibits the Metastasis of Triple-negative Breast Cancer Cells into the Lungs of SCID Mice FIG. 9 shows that monoclonal antibody 4C5 inhibits metastasis of MBDAMB231 triple-negative breast cancer cells in the lungs of SCID mice by 60%. In the experiment shown in FIG. 9, SCID female mice aged 6-8 weeks were injected intravenously with 5×105 DiI-labeled MDAMB231 breast cancer cells. One day post-injection the mice were split in 2 groups; 5 mice received 200 μg PBS buffer containing an irrelevant antibody intraperitoneally, daily for 2 weeks (control group), while 5 mice received 200 μg mAb 4C5 per mouse intraperitoneally, daily for 2 weeks (experimental group, see Methods). At the end of the experiment (day 72) lungs were obtained, counter-stained with Topro-3 and visualized by confocal microscopy. Under these conditions mAb 4C5 inhibited MDAMB231 metastasis by 38% ($p<0.05$).

Example 10

Figure 10:
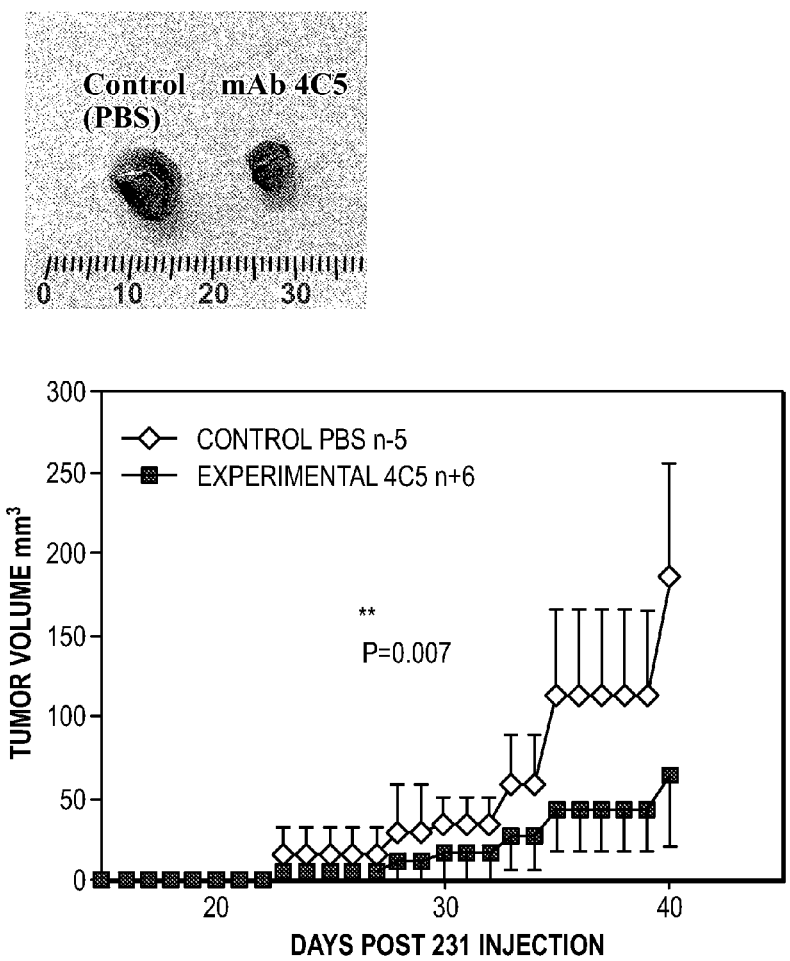
FIG. 10 shows that monoclonal Ab 4C5 delays primary tumor growth of MDAMB231 triple negative breast cancer cells growing orthotopically in SCID mice.

Monoclonal Ab 4C5 Delays Primary Tumor Growth of MDAMB231 Triple Negative Breast Cancer Cells Growing Orthotopically in SCID Mice To assess the effect of mAb 4C5 on orthotopic primary breast cancer growth, female SCID mice aged 6-8 weeks were injected under the mammary fat pad with $5 \times 10^6$ MDAMB231 triple-negative breast cancer cells. One day post-injection the mice were split in 2 groups; 5 mice received 200 μg PBS buffer containing an irrelevant antibody intraperitoneally, daily for 2 weeks (control group), while 6 mice received 200 μg mAb 4C5 per mouse intraperitoneally, daily for 2 weeks (experimental group, see Methods). Both groups were then left untreated until the end of the experiment (day 40). The results from a representative experiment shown in FIG. 10 suggest that mAb 4C5 inhibits the primary tumor growth of MDAMB231 cells by 65% ($p=0.007$).

The results described above were obtained using the following methods and materials.

RNA and DNA Manipulations.

Total RNA was isolated from $10^7$ hybridoma cells, using absorption on silica-based fiber matrix following the manufactures instructions (Absolutely RNA Mini Prep kit obtained from Stratagene). For Northern blot analysis, 25 ug RNA were separated by electrophoresis on agarose gel, transferred to a positively charged nylon membrane (Zeta-Probe obtained from Biorad) and hybridized with a labeled 1.2-kb heavy chain IgG1a cDNA probe. For amplification of the $V_H$ and $V_L$ antibody fragments, specific first strand cDNAs were synthesized by reverse transcription and using polyT oligonucleotide as primer, according to the manufacturer's instructions ($I^S$ Strand cDNA Synthesis kit for RT-PCR obtained from Roche). The cDNAs were subsequently amplified by PCR, using specific mouse immunoglobulin primers as shown in table 1.

TABLE 1

Murine IgG 1 Immunoglobulin PCR Primers
(SEQ ID NOS 11-21, respectively,
in order of appearance)

Heavy-chain Fd 3' primer

H3: 5'-AGG CTT ACT AGT ACA ATC CCT GGG CAC AAT-3'

Heavy-chain variable 5' primers

H5'1: 5'-AGG TCC AGC TGC TCG AGT CTG G-3'

H5'2: 5'-AGG TCC AGC TGC TCG AGT CAG G-3'

H5'3: 5'-AGG TCC AGC TTC TCG AGT CTG G-3'

TABLE 1-continued

Murine IgG 1 Immunoglobulin PCR Primers
(SEQ ID NOS 11-21, respectively,
in order of appearance)

H5'4: 5'-AGG TCC AGC TTC TCG AGT CAG G-3'

H5'5: 5'-AGG TCC AAC TGC TCG AGT CTG G-3'

H5'6: 5'-AGG TCC AAC TGC TCG AGT CAG G-3'

H5'7: 5'-AGG TCC AAC TTC TCG AGT CTG G-3'

H5'8: 5'-AGG TCC AAC TTC TCG AGT CAG G-3'

Murine κ light-chain 3' primer

L3': 5'-GCG CCG TCT AGA ATT AAC ACT CAT TCC TGT TGA A-3'

Murine light-chain variable 5' primers

L5'6: 5'-CCA GAT GTG AGC TCG TCA TGA CCC AGT CTC CA-3'

Amplified L-chain cDNA fragment was inserted into the SacI/XbaI restriction sites of the pComb3HSS phagemid (generous gift of Drs. C. F. Barbas and D. R. Burton, The Scripps Research Institute, La Jolla, Calif.) and sequenced in both directions at the sequence facility of the Institute of Molecular Biology and Biotechnology (IMBB). The germline counterpart of the rearranged $V_L$ sequence was analyzed using the National Center for Biotechnology Information IgBLAST server (http://www.ncbi.nlm.nih.gov/igblast) and the sequence was aligned using ClustalW software. Construction of mouse-human chimeric Ab 4C5

The mouse-human chimeric antibody was constructed by fusing the mAb 4C5 $V_L$ cDNA to a human $C_K$ gene segment. Briefly, the κ light chain of mAb 4C5 was subcloned into pBluescript SK-plasmid, and then the BsgI/XbaI fragment containing the mouse $C_K$ region was replaced by the BsgI/XbaI restriction fragment containing the human $C_K$. Finally, the chimeric κ L-chain gene of mAb 4C5 was inserted into the SacI/XbaI sites of pComb3HSS. All DNA manipulations were performed according to (Sambrook, J., et al, Molecular Cloning: A Laboratory Manual, Cold Spring Harbor Laboratory Press, Cold Spring Harbor, N.Y. 1989).

Expression and Purification of the Mouse and Chimeric L-chains

Soluble recombinant antibody light chains were produced from individual bacterial colonies as described previously (Barbas, C. F. 3 and Burton, D. R., Monoclonal Antibodies from Combinatorial Libraries, 1994) and the bacterial periplasmic fractions were extracted according to (Charlton, K. A., Expression and Isolation of Recombinant Antibody Fragments in *E. coli*., Methods Mol. Biol. 2004; 248:245-54) and purified by affinity chromatography using a Protein L column (PIERCE, USA) on an FPLC AKTA system (Amersham Biosciences, Piscataway, N.J.), according to the manufacture's instructions.

Reducing and Non Reducing SDS-PAGE

Antibody-containing FPLC fractions were pooled together and concentrated by centrifugation through a dialysis membrane (Amicon Ultra centrifugal filter devices obtained from Millipore). The electrophoretic motilities of the mouse, recombinant, and chimeric antibodies were tested under reducing and non-reducing conditions using the Laemmli discontinuous system as described before (Laemmli, U.K., Cleavage of Structural Proteins During the Assembly of the Head of Bacteriophage T4., Nature. 1970; 227: 680-5). Antibodies were visualized either by Coomasie-R stain or by western blot using specific secondary HRP-conjugated anti-kappa chain antibodies.

Preparation of cell lysates, immunoprecipitation and western blot analysis MDAMB453 cancer cell lysates were obtained and quantified as previously described (Thomaidou, D. and Patsavoudi, E., Identification of a Novel Neuron-specific Surface Antigen in the Developing Nervous System, by Monoclonal Antibody 4C5., Neuroscience. 1993; 53: 813-27), and equal amounts of total protein were subjected to SDS-PAGE and transferred onto nitrocellulose. The membranes were blotted for 40 min at room temperature with non-fat dry milk (5%) in tris-buffered saline ("TBS") containing 0.05% Tween-20, to block non-specific binding sites and were then incubated with the specific primary antibodies overnight at 4° C. The membranes were washed with 0.3% bovine serum albumin ("BSA") in TBS and incubated with horseradish peroxidase-labeled anti-kappa chain secondary antibodies for 2 hours at room temperature. After washing with TBS, the bound antibody complexes were detected using DAB or/and a chemiluminescence reagent (ECL chemiluminescence reagent obtained from Amersham) and exposure to X-ray film (XOMAT-AR film obtained from Kodak) as described by the manufacturers.

Immunoprecipitation was performed as previously described (Sidera, K. et al., A Critical role for HSP-90 in Cancer Cell Invasion Involves Interaction with the Extracellular Domain of HER-2., J. Biol. Chem., 2008; 283: 2031-41). In brief, equal amounts of pre-cleared MDAMB453 cancer cell lysates were incubated with antibodies overnight at 4° C. The immunocomplexes were then incubated for 2 hours at room temperature with protein G-sepharose, and washed 3 times with lysis buffer. Bound proteins were analyzed by gel electrophoresis followed by western blot. For all immunoprecipitation experiments, negative controls were performed using irrelevant IgGs.

Cell Cultures and Immunofluorescence

MDAMB453 breast cancer cell line was maintained in RPMI supplemented with 10% fetal bovine serum ("FBS"). For immunofluorescence studies, cells were plated on poly-L-lysine coated coverslips, at a density of $5 \times 10^4$ cells/well in a 48-well plate and cultured in RPMI medium supplemented with 10% FBS. After 24 h, cells were fixed and processed for indirect immunoflorescence, as previously described (Thomaidou, D. and Patsavoudi, E., Identification of a Novel Neuron-specific Surface Antigen in the Developing Nervous System, by Monoclonal Antibody 4C5., Neuroscience. 1993; 53: 813-27). Live MDAMB453 cells were labeled by indirect immunofluorescence as previously reported (Sidera, K. et al, Involvement of Cell Surface HSP90 in Cell Migration Reveals a Novel Role in the Developing Nervous System., J. Biol. Chem., 2004; 279: 45379-88). Alexa546-labeled phalloidin (Molecular Probes, Eugene, Oreg.) was used to visualize F-actin. For all experiments, controls were performed by omitting the primary antibodies or/and by using an IgG2a monoclonal antibody against the unrelated neuronal protein BM88. Immunofluorescence was analyzed by confocal microscopy using a Leica TSC confocal microscope.

Antibody Internalization Assay

MDAMB453 cells were incubated while in culture with the antibodies at equal concentrations for 2, 8 and 24 h. The cells were then washed in RPMI and fixed. For detection of any internalized antibody, cells were permeabilized with 0.1% Triton X-100 in PBS and subsequently incubated with Alexa488-conjugated secondary antibody (Molecular Probes, Eugene, Oreg.). For all experiments, controls were performed as mentioned above.

Wound Healing Assay

The assay was performed as previously described (Sidera, K. et al., A Critical role for HSP-90 in Cancer Cell Invasion Involves Interaction with the Extracellular Domain of HER-2., J. Biol. Chem., 2008; 283: 2031-41). Briefly, MDAMB453 and B16 F 10 were plated on poly-L-lysine coated cover slips in a 48-well plate at a density of $1 \times 10^5$ and $2.5 \times 10^5$ cells/well, respectively. After 24 hours the medium was changed to serum free RPMI and 16 hours later, a cell free area was generated by gently scratching the cell monolayer with a sterile yellow Gilson-pipette tip, thus resulting in the formation of an approximately 1 mm-wide cell-free area. Immediately after scratching, the medium was replaced with fresh medium, containing anti-HSP90α antibody, mAb 4C5, recombinant 4C5, or chimeric 4C5. All agents were maintained in the culture for the duration of the assay.

Control cultures were grown either in culture medium alone (RPMI) or in culture medium containing an IgG2a monoclonal antibody (concentrated serum free hybridoma supernatant), against the unrelated protein BM88. Migration of cancer cells within the gap was monitored microscopically at given time intervals, using a Leica DM IL inverted microscope, equipped with a LEICA DM300 video camera connected to a computer. Migration distance was estimated by acquiring and analyzing digital images, using the Image Pro Plus analysis software and expressed as the percent distance covered by cells in control cultures. Statistical analysis was performed by using the Student's T-test.

Trypan Blue Staining.

At the end point of the wound-healing assay, MDAMB453 cells were incubated for 5 min with 0.4% trypan blue in PBS. Excess staining was removed and cells were visualized in a Leica microscope.

Clonogenic Assay

Clonogenic assay was performed as previous described (Franken N et al., Clonogenic assay of cells in vitro Nature Protocols 2006; 1; 2315-2319). Briefly, MDAMB231 single cell suspensions were seeded on 6-well plates at a density of 500 cells/well and cultured either in culture medium alone or in culture medium containing 200 µg/ml chimeric 4C5. Media were replaced every 3 days and colonies were left to grow for 2 weeks before staining with Giemsa.

Assay of Breast Cancer Cell Metastatic Deposit and Metastasis in Lung Tissue

SCID mice originally purchased from Jackson Laboratory or Harlan Labs were bred and maintained under specific pathogen free conditions at the Experimental Animal Unit of the Hellenic Pasteur Institute. All of the experiments with animals were done in accordance with the guidelines approved by the Ethical Committee of the Hellenic Pasteur Institute. The in vivo metastatic deposit formation assay was performed as follows. Briefly, cultured MDAMB453 or MDAMB231 cells were pre-incubated with DiI for 1 hour, washed twice with PBS, trypsinized and made up to the cell density of $10^6/300$ µL in PBS in the absence or presence of 100 µg/ml of an irrelevant antibody BM88 (Patsavoudi E, Hurel C, Matsas R: Purification and characterization of neuron-specific surface antigen defined by monoclonal antibody BM88. J Neurochem 1991, 56:782-8) or 100 µg/ml of mAb 4C5. Twenty 8-10-week-old female SCID mice were injected through the tail vein with 0.3 ml of the above cell preparations. The animals were divided into two equal groups: the control group injected with cells dialysed in PBS or the irrelevant antibody and the mAb 4C5 treated group. The animals were euthanized 24 hours later (FIG. 8-metastatic deposits) or 72 days later (FIG. 9, lung metastasis assay). (In the metastatic deposit assays, a peristaltic pump was additionally connected to the left ventricle of the heart was employed to wash out the remaining blood from mouse lungs, by pumping 200 ml of saline buffer. This procedure ensures that all cancer cells which are not attached, either on the inner surface of the blood vessels or on the lung tissue, are removed.) Finally the lungs were perfused with 4% formalin solution and then embedded in OCT solution in order to perform cryosections. Each lung was sectioned with the cryotome and each section was counter stained with Dapi and visualised with a confocal microscope. In ten randomly chosen slides covering the whole of the lung tissue the MDAMB453 cells were calculated. The same experiment was performed twice with similar results.

Orthotopic Breast Cancer Mouse Xenograft Studies

The orthotopic breast cancer xenograft tumor mouse model was performed as previously described (Wei Yan et al The journal of Biological Chemistry vol 285 No. 18, pp 14042-14051, Apr. 30, 2010). Briefly, cultured MDAMB231 cells were pre-incubated with DiI for 1 hour, washed twice with PBS, collected with cell scraper and made up to the cell density of $5×10^6/100$ μL in PBS free of calcium and magnesium. Six to eight week-old female Balb-c SCID mice were injected under the mammary fat pad with $5×10^6$ DiI stained MDAMB231 cells and subsequently divided into 2 groups, experimental and control. One day after injection experimental mice received 200 μg mAb 4C5 (1 μg/μl) i.p. daily for 2 weeks whereas control mice received the same volume of vehicle (PBS). Tumor growth rate was monitored at weekly intervals and calculated based on the equation, tumor volume $(mm^3)$=length×width$^2$×0.52. At the end of the experiment animals were sacrificed and mouse tumor samples and samples from the lung and the liver were processed for immunohistochemistry.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

Incorporation by Reference

The entire contents of all patents published patent applications and other references cited herein are hereby expressly incorporated herein in their entireties by reference.

Equivalents

Those skilled in the art will recognize, or be able to ascertain using no more than routine experimentation, numerous equivalents to the specific procedures described herein. Such equivalents are considered to be within the scope of this invention and are covered by the following claims.

SEQUENCE LISTING

The Sequence Listing, SEQ ID NO: 1, corresponds to the nucleotide sequence encoding mAb 4C5.
GAGCTCGTCATGACCCAGTCTCCATCTTCCATGTATGCATCTCTAGGAGA

GAGAGTCACTATCACTTGCAAGGCGAGTCAGGACATTAATAGCTATTTAA

GCTGGTTCCAGCAGAAACCAGGGAAATCTCCTAAGACCCTGATCTATCGT

GCAAACAGATTGGTAGATGGGGTCCCATCAAGGTTCAGTGGCAGTGGATC

TGGGCAAGATTATTCTCTCACCATCAACAGCCTGGAGTATGAAGATATGG

GAATTTATTATTGTCTACAGTATGATGAGTTTCCTCGGCTCACGTTCGGT

GCTGGGACCAGGCTGGAGCTGAAACGGGCTGATGCTGCACCAACTGTATC

CATCTTCCCACCATCCAGTGAGCAGTTAACATCTGGAGGTGCCTCAGTCG

TGTGCTTCTTGAACAACTTCTATCCC    AAAGACATCAATGTCAAGTG

GAAGATTGATGGCAGTGAACGACAAAATGGCGTCCTGAACAGTTGGACTG

ATCAGGACAGCAAAGACAGCACCTACAGCATGAGCAGCACCCTCACGTTG

ACCAAGGACGAGTATGAACGACATAACAGCTATACCTGTGAGGCCACTCA

CAAGACATCAACTTCACCCATTGTCAAGAGCTTCAACAGGAATGAGTGT

The Sequence Listing, SEQ ID NO: 2, corresponds to the amino acid sequence of mAb 4C5.
ELVMTQSPSSMYASLGERVTITCKASQDINSYLSWFQQKPGKSPKTLIYR

ANRLVDGVPSRFSGSGSGQDYSLTINSLEYEDMGIYYCLQYDEFPRLTFG

AGTRLELKRADAAPTVSIFPPSSEQLTSGGASVVCFLNNFYPKDINVKWK

IDGSERQNGVLNSWTDQDSKDSTYSMSSTLTLTKDEYERHNSYTCEATHK

TSTSPIVKSFNRNEC

The Sequence Listing, SEQ ID NO: 3, corresponds to the nucleotide sequence of chimeric 4C5.
GAGCTCGTCATGACCCAGTCTCCATCTTCCATGTATGCATCTCTAGGAGA

GAGAGTCACTATCACTTGCAAGGCGAGTCAGGACATTAATAGCTATTTAA

GCTGGTTCCAGCAGAAACCAGGGAAATCTCCTAAGACCCTGATCTATCGT

GCAAACAGATTGGTAGATGGGGTCCCATCAAGGTTCAGTGGCAGTGGATC

TGGGCAAGATTATTCTCTCACCATCAACAGCCTGGAGTATGAAGATATGG

GAATTTATTATTGTCTACAGTATGATGAGTTTCCTCGGCTCACGTTCGGT

GCTGGGACCAGGCTGGAGCTGAAACGAACTGTGGCTGCACCATCTGTCTT

CATCTTCCCGCCATCTGATGAGCAGTTGAAATCTGGGACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGTTCGCCCGTCACAAAGAGCTTCAACAGGGAGAGTGT

The Sequence Listing, SEQ ID NO: 4, corresponds to the amino acid sequence of chimeric 4C5 and of ch4C5ΔCys (the latter however lacks the undelined C-terminal cysteine at the 3' end)
ELVMTQSPSSMYASLGERVTITCKASQDINSYLSWFQQKPGKSPKTLIYR

ANRLVDGVPSRFSGSGSGQDYSLTINSLEYEDMGIYYCLQYDEFPRLTFG

AGTRLELKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGE<u>C</u>

The Sequence Listing, SEQ ID NO: 5, corresponds to the amino acid sequence of CDR1 of 4C5:
KASQDINSYLS

SEQUENCE LISTING

The Sequence Listing, SEQ ID NO: 6, corresponds to the amino acid sequence of CDR2 of 4C5:
RANRLVD The Sequence Listing, SEQ ID NO: 7, corresponds to the amino acid sequence of CDR3 of 4C5:
LQYDEFPRLT The Sequence Listing, SEQ ID NO: 9, corresponds to the nucleotide sequence of chimeric 4C5 for improved expression in bacterial cells.
GAGCTCGTCATGACCCAGAGCCCGAGCAGCATGTATGCAAGCCTGGGCGA

ACGTGTGACCATCACCTGCAAAGCGAGCCAGGATATTAATAGCTATCTGT

CTTGGTTTCAGCAGAAACCGGGCAAAAGCCCGAAAACCCTGATTTATCGT

GCAAACCGTCTGGTAGATGGCGTGCCGTCACGTTTTAGCGGTTCTGGCAG

CGGCCAGGATTATAGCCTGACCATTAACAGCCTGGAATATGAAGATATGG

GCATTTATTATTGCCTGCAGTATGATGAATTTCCGCGTCTGACGTTTGGC

GCGGGCACCCGTCTGGAACTGAAACGTACCGTTGCGGCACCGAGCGTGTT

TATTTTTCCGCCGAGCGATGAACAGCTGAAAAGTGGCACCGCGAGCGTTG

TGTGCCTGCTGAATAACTTTTATCCGCGTGAAGCCAAAGTACAGTGGAAA

GTGGATAACGCCCTGCAGAGCGGCAACAGCCAGGAAAGCGTGACCGAACA

GGATAGCAAAGATAGCACCTATAGCCTGTCTAGCACCCTGACGCTGAGCA

AAGCAGATTATGAAAAACATAAAGTGTATGCCTGCGAAGTGACCCATCAG

GGCCTGAGCAGCCCGGTGACCAAAAGCTTTAATCGTGGCGAATGC

The Sequence Listing, SEQ ID NO: 10, corresponds to the nucleotide sequence of chimeric 4C5 for improved expression in bacterial cells.
GAGCTCGTCATGACCCAGAGCCCGAGCAGCATGTATGCAAGCCTGGGCGA

ACGTGTGACCATCACCTGCAAAGCGAGCCAGGATATTAATAGCTATCTGT

CTTGGTTTCAGCAGAAACCGGGCAAAAGCCCGAAAACCCTGATTTATCGT

GCAAACCGTCTGGTAGATGGCGTGCCGTCACGTTTTAGCGGTTCTGGCAG

CGGCCAGGATTATAGCCTGACCATTAACAGCCTGGAATATGAAGATATGG

GCATTTATTATTGCCTGCAGTATGATGAATTTCCGCGTCTGACGTTTGGC

GCGGGCACCCGTCTGGAACTGAAACGTACCGTTGCGGCACCGAGCGTGTT

TATTTTTCCGCCGAGCGATGAACAGCTGAAAAGTGGCACCGCGAGCGTTG

TGTGCCTGCTGAATAACTTTTATCCGCGTGAAGCCAAAGTACAGTGGAAA

GTGGATAACGCCCTGCAGAGCGGCAACAGCCAGGAAAGCGTGACCGAACA

GGATAGCAAAGATAGCACCTATAGCCTGTCTAGCACCCTGACGCTGAGCA

AAGCAGATTATGAAAAACATAAAGTGTATGCCTGCGAAGTGACCCATCAG

GGCCTGAGCAGCCCGGTGACCAAAAGCTTTAATCGTGGCGAA

What is claimed is:

1. An isolated chimeric antibody comprising the sequence of SEQ ID NO: 4, wherein the chimeric antibody has a murine kappa L-chain that lacks heavy chains, wherein the murine immunoglobulin κ light chain constant domain ($C_K$) is replaced with the corresponding human $C_K$ domain or a fragment thereof, and wherein the antibody specifically binds HSP90 and is capable of reducing the growth and/or the invasiveness of a neoplastic cell.

2. The chimeric antibody of claim 1, wherein the antibody is a humanized antibody or is isolated from a culture of prokaryotic or eukaryotic cells.

3. The chimeric antibody of claim 1, wherein the antibody is a monomer, a dimer or a multimer.

4. The chimeric antibody of claim 1, wherein the chimeric antibody has a reduced capacity to induce an immune response in a human subject, relative to a conventional murine antibody.

5. The chimeric antibody of claim 1, wherein the ability of the antibody or a fragment thereof to reduce growth and invasiveness is assayed using a cancer cell clonogenic assay, a wound healing assay, a lung metastatic deposit formation assay, a lung metastasis inhibition assay, a breast cancer primary tumor growth inhibition assay, by detecting actin rearrangement, by detecting lamellipodia development, or by detecting another morphological marker of invasiveness, by detecting inhibition of metastatic lung deposits, by detecting inhibition of lung metastasis, by detecting delay of primary growth tumors implanted orthotopically in mouse fat pads, or by detecting another marker of efficacy, respectively.

6. An isolated polypeptide comprising the sequence of SEQ ID NO: 4.

7. An isolated polynucleotide encoding the chimeric antibody of claim 1.

8. An isolated polynucleotide encoding the isolated polypeptide of claim 6.

9. An expression vector comprising the polynucleotide of claim 7 positioned for expression in a cell.

10. A cell comprising the expression vector of claim 9.

11. The cell of claim 10, wherein the cell is a prokaryotic or eukaryotic cell.

12. A method for producing a chimeric antibody of claim 1, the method comprising culturing the cell of claim 10 under conditions suitable for expression of the chimeric antibody, and isolating the chimeric antibody from the cultured cell.

13. A pharmaceutical composition for the treatment of neoplasia comprising a therapeutically effective amount of the chimeric antibody of claim 1.

14. A pharmaceutical composition for the treatment of neoplasia comprising a therapeutically effective amount of the isolated polypeptide of claim 6.

15. A kit for the treatment of a neoplasia, the kit comprising a therapeutically effective amount of the chimeric antibody of claim 1.

16. An isolated chimeric antibody comprising an amino acid sequence having at least 90% or 95% identity to SEQ ID NO: 4, wherein the chimeric antibody has a murine kappa L-chain, wherein the murine immunoglobulin κ light chain constant domain ($C_K$) is replaced with the corresponding human $C_K$ domain or a fragment thereof, wherein the antibody specifically binds HSP90 and is capable of reducing the growth and/or the invasiveness of a neoplastic cell, and wherein the antibody comprises the complimentarity determining regions of SEQ ID NO: 5, SEQ ID NO: 6, and SEQ ID NO: 7.

17. The isolated chimeric antibody of claim 16, wherein the amino acid sequence has at least 95% identity to the sequence of SEQ ID NO: 4.

18. The chimeric antibody of claim 16, wherein the antibody is a monomer, a dimer or a multimer.

19. An isolated polynucleotide encoding the chimeric antibody of claim 16.

20. An expression vector comprising the polynucleotide of claim 19 positioned for expression in a cell.

21. A cell comprising the expression vector of claim 20.

22. The cell of claim 21, wherein the cell is a prokaryotic or eukaryotic cell.

* * * * *